United States Patent
Renock

(10) Patent No.: US 11,980,679 B2
(45) Date of Patent: May 14, 2024

(54) SULFATE FREE COMPOSITION WITH ENHANCED DEPOSITION OF SCALP ACTIVE

(71) Applicant: The Procter & Gamble Company, Cincinnati, OH (US)

(72) Inventor: Sean Michael Renock, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 17/111,919

(22) Filed: Dec. 4, 2020

(65) Prior Publication Data

US 2021/0169765 A1    Jun. 10, 2021

Related U.S. Application Data

(60) Provisional application No. 62/944,685, filed on Dec. 6, 2019.

(51) Int. Cl.
| | |
|---|---|
| *A61K 8/46* | (2006.01) |
| *A61K 8/34* | (2006.01) |
| *A61K 8/368* | (2006.01) |
| *A61K 8/37* | (2006.01) |
| *A61K 8/49* | (2006.01) |
| *A61K 8/58* | (2006.01) |
| *A61K 8/73* | (2006.01) |
| *A61K 8/81* | (2006.01) |
| *A61K 8/891* | (2006.01) |
| *A61Q 5/00* | (2006.01) |
| *A61Q 5/12* | (2006.01) |

(52) U.S. Cl.
CPC ............ *A61K 8/466* (2013.01); *A61K 8/347* (2013.01); *A61K 8/368* (2013.01); *A61K 8/37* (2013.01); *A61K 8/4926* (2013.01); *A61K 8/4946* (2013.01); *A61K 8/58* (2013.01); *A61K 8/737* (2013.01); *A61K 8/8129* (2013.01); *A61K 8/891* (2013.01); *A61Q 5/006* (2013.01); *A61Q 5/12* (2013.01); *A61K 2800/33* (2013.01); *A61K 2800/48* (2013.01)

(58) Field of Classification Search
CPC ...... A61K 8/466; A61K 8/8129; A61K 8/737; A61K 8/891; A61K 8/58; A61K 8/4926; A61K 2800/48; A61K 8/368; A61K 8/347; A61K 8/37; A61K 2800/33; A61K 8/4946; A61Q 5/12; A61Q 5/006
See application file for complete search history.

(56) References Cited

U.S. PATENT DOCUMENTS

| | | |
|---|---|---|
| 1,489,388 A | 4/1924 | Glenn |
| 1,600,340 A | 9/1926 | Hoffman |
| 1,612,255 A | 12/1926 | William |
| 2,438,091 A | 3/1948 | Lynch |
| 2,528,378 A | 10/1950 | Mannheimer |
| 2,658,072 A | 11/1953 | Milton |
| 2,809,971 A | 10/1957 | Jack et al. |
| 2,879,231 A | 3/1959 | Marshall |
| 3,219,656 A | 11/1965 | Boettner |
| 3,236,733 A | 2/1966 | Karsten et al. |
| 3,373,208 A | 3/1968 | Blumenthal |
| 3,636,113 A | 1/1972 | Hall |
| 3,709,437 A | 1/1973 | Wright |
| 3,716,498 A | 2/1973 | Hall |
| 3,753,196 A | 8/1973 | Kurtz et al. |
| 3,761,418 A | 9/1973 | Parran |
| 3,792,068 A | 2/1974 | Luedders et al. |
| 3,887,692 A | 6/1975 | Gilman |
| 3,904,741 A | 9/1975 | Jones et al. |
| 3,950,532 A | 4/1976 | Bouillon et al. |
| 3,959,160 A | 5/1976 | Horsler et al. |
| 4,049,792 A | 9/1977 | Elsnau |
| 4,089,945 A | 5/1978 | Brinkman et al. |
| 4,120,948 A | 10/1978 | Shelton |
| 4,137,180 A | 1/1979 | Naik |
| 4,237,155 A | 12/1980 | Kardouche |
| 4,309,119 A | 1/1982 | Wittersheim |
| 4,323,683 A | 4/1982 | Bolich, Jr. et al. |
| 4,329,334 A | 5/1982 | Su et al. |
| 4,345,080 A | 8/1982 | Bolich, Jr. |

(Continued)

FOREIGN PATENT DOCUMENTS

| | | |
|---|---|---|
| BE | 825146 A | 8/1975 |
| BR | 199400875 A | 10/1995 |

(Continued)

OTHER PUBLICATIONS

BASF, "Practical Guide to Rheology Modifiers", download from https://insights.basf.com/files/BASF_ED_RheologyModifiers_download.pdf on Nov. 1, 2022. (Year: 2022).*

(Continued)

*Primary Examiner* — Jianfeng Song
(74) *Attorney, Agent, or Firm* — Linda M. Sivik

(57) ABSTRACT

The present invention is directed to a personal care composition comprising from about 15% to about 22% of one or more sulfate free surfactants; from about 0.1% to about 10% of one or more scalp active; from about 0.1% to about 1.2% of a cationic polymers having a molecular weight in the range of 50,000 to less than or equal to 1.8 million and a charge density of about 0.5 to about 1.7 meq/g, from about 0.1% to about 1.2% of a rheology modifier and having a pH of about 5 to about 7 and having a viscosity of >about 5000 cps.

24 Claims, No Drawings

(56) References Cited

U.S. PATENT DOCUMENTS

| | | |
|---|---|---|
| 4,359,456 A | 11/1982 | Gosling et al. |
| 4,379,753 A | 4/1983 | Bolich, Jr. |
| 4,430,243 A | 2/1984 | Bragg |
| 4,470,982 A | 9/1984 | Winkler |
| 4,726,945 A | 2/1988 | Patel |
| 4,732,696 A | 3/1988 | Urfer |
| 4,839,166 A | 6/1989 | Grollier et al. |
| 4,854,333 A | 8/1989 | Inman et al. |
| 4,867,971 A | 9/1989 | Ryan et al. |
| 4,931,274 A | 6/1990 | Barabino et al. |
| 4,973,416 A | 11/1990 | Kennedy |
| 4,985,238 A | 1/1991 | Tanner et al. |
| 4,997,641 A | 3/1991 | Hartnett |
| 5,019,375 A | 5/1991 | Tanner et al. |
| 5,093,112 A | 3/1992 | Birtwistle et al. |
| 5,104,646 A | 4/1992 | Bolich, Jr. |
| 5,106,609 A | 4/1992 | Bolich, Jr. |
| 5,135,747 A | 8/1992 | Faryniarz et al. |
| 5,156,834 A | 10/1992 | Beckmeyer et al. |
| 5,294,644 A | 3/1994 | Login et al. |
| 5,296,157 A | 3/1994 | Macgilp et al. |
| 5,296,622 A | 3/1994 | Uphues |
| 5,298,640 A | 3/1994 | Callaghan et al. |
| 5,332,569 A | 7/1994 | Wood et al. |
| 5,364,031 A | 11/1994 | Taniguchi et al. |
| 5,374,421 A | 12/1994 | Tashiro |
| 5,374,614 A | 12/1994 | Behan et al. |
| 5,409,695 A | 4/1995 | Abrutyn et al. |
| 5,415,810 A | 5/1995 | Lee et al. |
| 5,417,965 A | 5/1995 | Janchitraponvej et al. |
| 5,429,816 A | 7/1995 | Hofrichter et al. |
| 5,439,682 A | 8/1995 | Wivell |
| 5,441,659 A | 8/1995 | Minor |
| 5,486,303 A | 1/1996 | Capeci |
| 5,489,392 A | 2/1996 | Capeci |
| 5,496,488 A | 3/1996 | Kacher et al. |
| 5,516,448 A | 5/1996 | Capeci |
| 5,536,493 A | 7/1996 | Dubief |
| 5,554,588 A | 9/1996 | Behan et al. |
| 5,560,918 A | 10/1996 | Wivell |
| 5,565,422 A | 10/1996 | Del |
| 5,569,645 A | 10/1996 | Dinniwell |
| 5,574,005 A | 11/1996 | Welch |
| 5,576,282 A | 11/1996 | Miracle |
| 5,578,298 A | 11/1996 | Berthiaume |
| 5,595,967 A | 1/1997 | Miracle |
| 5,597,936 A | 1/1997 | Perkins |
| 5,599,549 A | 2/1997 | Wivell |
| 5,624,666 A | 4/1997 | Coffindaffer et al. |
| 5,635,469 A | 6/1997 | Fowler et al. |
| 5,665,267 A | 9/1997 | Dowell et al. |
| 5,691,297 A | 11/1997 | Nassano |
| 5,714,137 A | 2/1998 | Trinh |
| 5,747,436 A | 5/1998 | Patel |
| 5,776,444 A | 7/1998 | Birtwistle et al. |
| 5,800,897 A | 9/1998 | Sharma |
| 5,816,446 A | 10/1998 | Steindorf et al. |
| 5,830,440 A | 11/1998 | Sturla et al. |
| 5,853,618 A | 12/1998 | Barker |
| 5,879,584 A | 3/1999 | Bianchetti |
| 5,891,424 A | 4/1999 | Bretzler et al. |
| 5,902,225 A | 5/1999 | Monson |
| 5,925,603 A | 7/1999 | D Angelo |
| 5,942,217 A | 8/1999 | Woo et al. |
| 5,976,514 A | 11/1999 | Guskey et al. |
| 5,980,877 A | 11/1999 | Baravetto |
| 5,985,939 A | 11/1999 | Minor |
| 6,015,547 A | 1/2000 | Yam |
| 6,015,780 A | 1/2000 | Llosas Bigorra et al. |
| 6,020,303 A | 2/2000 | Cripe et al. |
| 6,039,933 A | 3/2000 | Samain et al. |
| 6,046,152 A | 4/2000 | Vinson et al. |
| 6,060,443 A | 5/2000 | Cripe et al. |
| 6,087,309 A | 7/2000 | Vinson et al. |
| 6,110,451 A | 8/2000 | Matz et al. |
| 6,133,222 A | 10/2000 | Vinson et al. |
| 6,139,828 A | 10/2000 | Mccullough |
| 6,153,567 A | 11/2000 | Hughes |
| 6,153,569 A | 11/2000 | Halloran |
| 6,162,834 A | 12/2000 | Sebillotte-Arnaud et al. |
| 6,180,121 B1 | 1/2001 | Guenin et al. |
| 6,225,464 B1 | 5/2001 | Hiler, II |
| 6,231,844 B1 | 5/2001 | Nambu |
| 6,232,302 B1 | 5/2001 | Alberico et al. |
| 6,248,135 B1 | 6/2001 | Trinh et al. |
| 6,268,431 B1 | 7/2001 | Snyder et al. |
| 6,284,225 B1 | 9/2001 | Bhatt |
| 6,329,331 B1 | 12/2001 | Aronson |
| 6,335,312 B1 | 1/2002 | Coffindaffer et al. |
| 6,352,688 B1 | 3/2002 | Scavone et al. |
| 6,386,392 B1 | 5/2002 | Argentieri |
| 6,413,920 B1 | 7/2002 | Bettiol |
| 6,423,305 B1 | 7/2002 | Cauwet-Martin et al. |
| 6,436,442 B1 | 8/2002 | Woo et al. |
| 6,451,300 B1 | 9/2002 | Dunlop et al. |
| 6,488,943 B1 | 12/2002 | Beerse et al. |
| 6,511,669 B1 | 1/2003 | Garnier et al. |
| 6,565,863 B1 | 5/2003 | Guillou et al. |
| 6,579,907 B1 | 6/2003 | Sebillotte-Arnaud et al. |
| 6,627,585 B1 | 9/2003 | Steer |
| 6,642,194 B2 | 11/2003 | Harrison |
| 6,649,155 B1 | 11/2003 | Dunlop et al. |
| 6,656,923 B1 | 12/2003 | Trinh |
| 6,660,288 B1 | 12/2003 | Behan et al. |
| 6,679,324 B2 | 1/2004 | Den et al. |
| 6,716,455 B2 | 4/2004 | Birkel |
| 6,716,805 B1 | 4/2004 | Sherry |
| 6,740,713 B1 | 5/2004 | Busch et al. |
| 6,743,760 B1 | 6/2004 | Hardy et al. |
| 6,764,986 B1 | 7/2004 | Busch et al. |
| 6,767,507 B1 | 7/2004 | Woo et al. |
| 6,794,356 B2 | 9/2004 | Turner |
| 6,814,088 B2 | 11/2004 | Barnabas et al. |
| 6,827,795 B1 | 12/2004 | Kasturi et al. |
| 6,869,923 B1 | 3/2005 | Cunningham |
| 6,897,253 B2 | 5/2005 | Schmucker-castner |
| 6,908,889 B2 | 6/2005 | Niemiec et al. |
| 6,930,078 B2 | 8/2005 | Wells |
| 6,992,054 B2 | 1/2006 | Lee et al. |
| 7,018,978 B2 | 3/2006 | Miracle et al. |
| 7,030,068 B2 | 4/2006 | Clare et al. |
| 7,100,767 B2 | 9/2006 | Chomik et al. |
| 7,151,079 B2 | 12/2006 | Fack et al. |
| 7,172,099 B2 | 2/2007 | Hoefte |
| 7,202,198 B2 | 4/2007 | Gordon et al. |
| 7,217,752 B2 | 5/2007 | Schmucker-Castner et al. |
| 7,220,408 B2 | 5/2007 | Decoster et al. |
| 7,223,361 B2 | 5/2007 | Kvietok |
| 7,223,385 B2 | 5/2007 | Gawtrey et al. |
| 7,485,289 B2 | 2/2009 | Gawtrey et al. |
| 7,504,094 B2 | 3/2009 | Decoster et al. |
| 7,531,497 B2 | 5/2009 | Midha et al. |
| 7,541,320 B2 | 6/2009 | Dabkowski et al. |
| 7,598,213 B2 | 10/2009 | Geary et al. |
| 7,659,233 B2 | 2/2010 | Hurley et al. |
| 7,666,825 B2 | 2/2010 | Wagner et al. |
| 7,820,609 B2 | 10/2010 | Soffin et al. |
| 7,829,514 B2 | 11/2010 | Paul et al. |
| 7,841,036 B2 | 11/2010 | Smith |
| 7,867,505 B2 | 1/2011 | Elliott et al. |
| 7,928,053 B2 | 4/2011 | Hecht et al. |
| 7,977,288 B2 | 7/2011 | SenGupta |
| 8,007,545 B2 | 8/2011 | Fujii et al. |
| 8,058,500 B2 | 11/2011 | Sojka et al. |
| 8,084,407 B2 | 12/2011 | Soffin et al. |
| 8,088,721 B2 | 1/2012 | Soffin et al. |
| 8,119,168 B2 | 2/2012 | Johnson |
| 8,124,063 B2 | 2/2012 | Harichian et al. |
| 8,158,571 B2 | 4/2012 | Alonso |
| 8,300,949 B2 | 10/2012 | Xu |
| 8,322,631 B2 | 12/2012 | Richardson et al. |
| 8,343,469 B2 | 1/2013 | Bierganns et al. |
| 8,349,300 B2 | 1/2013 | Wells |
| 8,357,359 B2 | 1/2013 | Woo et al. |

(56) References Cited

U.S. PATENT DOCUMENTS

| | | |
|---|---|---|
| 8,361,450 B2 | 1/2013 | Johnson et al. |
| 8,388,699 B2 | 3/2013 | Wood |
| 8,401,304 B2 | 3/2013 | Cavallaro et al. |
| 8,435,501 B2 | 5/2013 | Peffly et al. |
| 8,437,556 B1 | 5/2013 | Saisan |
| 8,491,877 B2 | 7/2013 | Schwartz et al. |
| 8,539,631 B2 | 9/2013 | Catalfamo et al. |
| 8,574,561 B1 | 11/2013 | Patel et al. |
| 8,580,725 B2 | 11/2013 | Kuhlman et al. |
| 8,609,600 B2 | 12/2013 | Warr et al. |
| 8,628,760 B2 | 1/2014 | Carter et al. |
| 8,629,095 B2 | 1/2014 | Deleersnyder |
| 8,653,014 B2 | 2/2014 | Hilvert |
| 8,675,919 B2 | 3/2014 | Maladen |
| 8,679,316 B2 | 3/2014 | Brunner et al. |
| 8,680,035 B2 | 3/2014 | Kuhlman et al. |
| 8,699,751 B2 | 4/2014 | Maladen |
| 8,709,337 B2 | 4/2014 | Gruenbacher et al. |
| 8,709,385 B2 | 4/2014 | Tamarkin |
| 8,741,275 B2 | 6/2014 | Dente et al. |
| 8,741,363 B2 | 6/2014 | Albrecht et al. |
| 8,771,765 B1 | 7/2014 | Fernandez |
| 8,772,354 B2 | 7/2014 | Williams et al. |
| 8,795,635 B2 | 8/2014 | Tamarkin et al. |
| 8,877,316 B2 | 11/2014 | Hasenoehrl et al. |
| 8,883,698 B2 | 11/2014 | Scheibel et al. |
| 8,931,711 B2 | 1/2015 | Gruenbacher |
| 8,980,239 B2 | 3/2015 | Staudigel et al. |
| 8,987,187 B2 | 3/2015 | Smets et al. |
| 9,006,162 B1 | 4/2015 | Rizk |
| 9,186,642 B2 | 11/2015 | Dihora et al. |
| 9,187,407 B2 | 11/2015 | Koshti et al. |
| 9,265,727 B1 | 2/2016 | Lowenborg |
| 9,272,164 B2 | 3/2016 | Johnson et al. |
| 9,296,550 B2 | 3/2016 | Smith |
| 9,308,398 B2 | 4/2016 | Hutton et al. |
| 9,393,447 B2 | 7/2016 | Zasloff |
| 9,428,616 B2 | 8/2016 | Wagner |
| 9,511,007 B2 | 12/2016 | Frantz et al. |
| 9,512,275 B2 | 12/2016 | Wagner |
| 9,610,239 B2 | 4/2017 | Feng |
| 9,655,821 B2 | 5/2017 | Carter et al. |
| 9,662,291 B2 | 5/2017 | Johnson et al. |
| 9,682,021 B2 | 6/2017 | Tamarkin et al. |
| 9,776,787 B2 | 10/2017 | Nakajima |
| 9,949,901 B2 | 4/2018 | Zhao et al. |
| 9,949,911 B2 | 4/2018 | Cetti |
| 9,968,535 B2 | 5/2018 | Kitko |
| 9,968,537 B2 | 5/2018 | Sharma |
| 9,993,419 B2 | 6/2018 | Glenn, Jr. et al. |
| 9,993,420 B2 | 6/2018 | Glenn, Jr. et al. |
| 10,039,706 B2 | 8/2018 | Meralli et al. |
| 10,039,939 B2 | 8/2018 | Xavier et al. |
| 10,113,140 B2 | 10/2018 | Frankenbach |
| 10,182,976 B2 | 1/2019 | Staudigel |
| 10,238,685 B2 | 3/2019 | Dunn et al. |
| 10,265,261 B2 | 4/2019 | Park et al. |
| 10,311,575 B2 | 6/2019 | Stofel |
| 10,392,625 B2 | 8/2019 | Jin et al. |
| 10,426,713 B2 | 10/2019 | Song |
| 10,441,519 B2 | 10/2019 | Zhao |
| 10,552,557 B2 | 2/2020 | Frankenbach et al. |
| 10,610,473 B2 | 4/2020 | Hertenstein et al. |
| 10,653,590 B2 | 5/2020 | Torres Rivera |
| 10,799,434 B2 | 10/2020 | Torres Rivera |
| 10,842,720 B2 | 11/2020 | Thompson |
| 10,881,597 B2 | 1/2021 | Lane et al. |
| 10,888,505 B2 | 1/2021 | Johnson |
| 10,912,732 B2 | 2/2021 | Gillis |
| 11,116,703 B2 | 9/2021 | Song et al. |
| 11,116,704 B2 | 9/2021 | Song et al. |
| 11,129,775 B2 | 9/2021 | Song et al. |
| 11,334,694 B2 | 5/2022 | Cetti et al. |
| 11,334,695 B2 | 5/2022 | Cetti et al. |
| 2001/0000467 A1 | 4/2001 | Murray |
| 2001/0006088 A1 | 7/2001 | Lyle |
| 2001/0006621 A1 | 7/2001 | Coupe et al. |
| 2001/0016565 A1 | 8/2001 | Bodet et al. |
| 2002/0012646 A1 | 1/2002 | Royce et al. |
| 2002/0028182 A1 | 3/2002 | Dawson |
| 2002/0037299 A1 | 3/2002 | Turowski-Wanke et al. |
| 2002/0172648 A1 | 11/2002 | Hehner et al. |
| 2002/0193265 A1 | 12/2002 | Perron et al. |
| 2002/0197213 A1 | 12/2002 | Schmenger et al. |
| 2003/0003070 A1 | 1/2003 | Eggers et al. |
| 2003/0008787 A1 | 1/2003 | Mcgee et al. |
| 2003/0022799 A1 | 1/2003 | Alvarado et al. |
| 2003/0049292 A1 | 3/2003 | Turowski-Wanke et al. |
| 2003/0050150 A1 | 3/2003 | Tanaka |
| 2003/0059377 A1 | 3/2003 | Riley |
| 2003/0083210 A1 | 5/2003 | Goldberg |
| 2003/0108501 A1 | 6/2003 | Hofrichter |
| 2003/0147842 A1 | 8/2003 | Restle et al. |
| 2003/0154561 A1 | 8/2003 | Patel |
| 2003/0161802 A1 | 8/2003 | Flammer |
| 2003/0180238 A1 | 9/2003 | Sakurai et al. |
| 2003/0180246 A1 | 9/2003 | Frantz et al. |
| 2003/0185867 A1 | 10/2003 | Kerschner et al. |
| 2003/0192922 A1 | 10/2003 | Ceppaluni et al. |
| 2003/0202952 A1 | 10/2003 | Wells et al. |
| 2003/0223951 A1 | 12/2003 | Geary et al. |
| 2003/0228272 A1 | 12/2003 | Amjad et al. |
| 2004/0014879 A1 | 1/2004 | Denzer et al. |
| 2004/0064117 A1 | 4/2004 | Hammons |
| 2004/0131660 A1 | 7/2004 | Lange et al. |
| 2004/0144863 A1 | 7/2004 | Kendrick |
| 2004/0151793 A1 | 8/2004 | Paspaleeva-kuhn et al. |
| 2004/0157754 A1 | 8/2004 | Geary et al. |
| 2004/0229963 A1 | 11/2004 | Stephane |
| 2004/0234484 A1 | 11/2004 | Peffly |
| 2004/0235689 A1 | 11/2004 | Sakai et al. |
| 2005/0003975 A1 | 1/2005 | Browne et al. |
| 2005/0003980 A1 | 1/2005 | Baker |
| 2005/0020468 A1 | 1/2005 | Frantz et al. |
| 2005/0136011 A1 | 6/2005 | Nekludoff |
| 2005/0152863 A1 | 7/2005 | Brautigam |
| 2005/0192207 A1 | 9/2005 | Morgan, III et al. |
| 2005/0201967 A1 | 9/2005 | Albrecht et al. |
| 2005/0202984 A1 | 9/2005 | Schwartz et al. |
| 2005/0208106 A1 | 9/2005 | Lange et al. |
| 2005/0227902 A1 | 10/2005 | Erazo-majewicz et al. |
| 2005/0233929 A1 | 10/2005 | Queen |
| 2005/0245407 A1 | 11/2005 | Ishihara |
| 2005/0276831 A1 | 12/2005 | Dihora |
| 2006/0002880 A1 | 1/2006 | Peffly |
| 2006/0005333 A1 | 1/2006 | Catalfamo et al. |
| 2006/0009337 A1 | 1/2006 | Smith |
| 2006/0030509 A1 | 2/2006 | Modi |
| 2006/0034778 A1 | 2/2006 | Kitano et al. |
| 2006/0057075 A1 | 3/2006 | Arkin et al. |
| 2006/0057097 A1 | 3/2006 | Derici |
| 2006/0079417 A1 | 4/2006 | Wagner |
| 2006/0079418 A1 | 4/2006 | Wagner et al. |
| 2006/0079419 A1 | 4/2006 | Wagner et al. |
| 2006/0079420 A1 | 4/2006 | Wagner et al. |
| 2006/0079421 A1 | 4/2006 | Wagner et al. |
| 2006/0084589 A1 | 4/2006 | Vlad et al. |
| 2006/0090777 A1 | 5/2006 | Hecht et al. |
| 2006/0094610 A1 | 5/2006 | Yamato et al. |
| 2006/0110415 A1 | 5/2006 | Gupta |
| 2006/0120982 A1 | 6/2006 | Derici et al. |
| 2006/0120988 A1 | 6/2006 | Bailey et al. |
| 2006/0135397 A1 | 6/2006 | Bissey-beugras |
| 2006/0166857 A1 | 7/2006 | Surburg et al. |
| 2006/0171911 A1 | 8/2006 | Schwartz et al. |
| 2006/0182703 A1 | 8/2006 | Arisz |
| 2006/0183662 A1 | 8/2006 | Crotty |
| 2006/0210139 A1 | 9/2006 | Carroll |
| 2006/0229227 A1 | 10/2006 | Goldman |
| 2006/0252662 A1 | 11/2006 | Soffin |
| 2006/0263319 A1* | 11/2006 | Fan ................. A61K 8/731 424/70.28 |
| 2006/0269503 A1 | 11/2006 | Yamazaki |
| 2006/0276357 A1 | 12/2006 | Smith, III et al. |

(56) References Cited

U.S. PATENT DOCUMENTS

| | | |
|---|---|---|
| 2006/0292104 A1 | 12/2006 | Guskey |
| 2007/0003499 A1 | 1/2007 | Shen et al. |
| 2007/0020263 A1 | 1/2007 | Shitara et al. |
| 2007/0072781 A1 | 3/2007 | Soffin et al. |
| 2007/0110700 A1 | 5/2007 | Wells |
| 2007/0154402 A1 | 7/2007 | Trumbore et al. |
| 2007/0155637 A1 | 7/2007 | Smith, III et al. |
| 2007/0160555 A1 | 7/2007 | Staudigel |
| 2007/0179207 A1 | 8/2007 | Fernandez de Castro et al. |
| 2007/0225193 A1 | 9/2007 | Kuhlman et al. |
| 2007/0269397 A1 | 11/2007 | Terada |
| 2007/0275866 A1 | 11/2007 | Dykstra |
| 2007/0292380 A1 | 12/2007 | Staudigel |
| 2007/0298994 A1 | 12/2007 | Finke et al. |
| 2008/0003245 A1 | 1/2008 | Kroepke et al. |
| 2008/0008668 A1 | 1/2008 | Harichian et al. |
| 2008/0019928 A1 | 1/2008 | Franzke |
| 2008/0063618 A1 | 3/2008 | Johnson |
| 2008/0138442 A1 | 6/2008 | Johnson |
| 2008/0152610 A1 | 6/2008 | Cajan |
| 2008/0160093 A1 | 7/2008 | Schwartz et al. |
| 2008/0176780 A1 | 7/2008 | Warr |
| 2008/0194454 A1 | 8/2008 | Morgan |
| 2008/0206179 A1 | 8/2008 | Peffly et al. |
| 2008/0229512 A1 | 9/2008 | Syed et al. |
| 2008/0260655 A1 | 10/2008 | Tamarkin et al. |
| 2008/0260665 A1 | 10/2008 | Guerchet et al. |
| 2008/0261844 A1 | 10/2008 | Ruppert et al. |
| 2008/0317698 A1 | 12/2008 | Wells et al. |
| 2009/0005280 A1 | 1/2009 | Woo et al. |
| 2009/0029900 A1 | 1/2009 | Cetti et al. |
| 2009/0041702 A1 | 2/2009 | Molenda |
| 2009/0062406 A1 | 3/2009 | Loeffler |
| 2009/0155383 A1 | 6/2009 | Kitko et al. |
| 2009/0178210 A1 | 7/2009 | Bistram |
| 2009/0197784 A1 | 8/2009 | Ainger |
| 2009/0221463 A1 | 9/2009 | Kitko et al. |
| 2009/0240223 A1 | 9/2009 | Warren |
| 2009/0246236 A1 | 10/2009 | Kitko |
| 2009/0312223 A1 | 12/2009 | Yang et al. |
| 2009/0312224 A1 | 12/2009 | Yang et al. |
| 2009/0324505 A1 | 12/2009 | Seidling |
| 2010/0000116 A1 | 1/2010 | Aouad et al. |
| 2010/0001116 A1 | 1/2010 | Johnson |
| 2010/0009285 A1 | 1/2010 | Daems et al. |
| 2010/0061946 A1 | 3/2010 | Scherner et al. |
| 2010/0087357 A1 | 4/2010 | Morgan, III et al. |
| 2010/0152083 A1 | 6/2010 | Velazquez |
| 2010/0168251 A1 | 7/2010 | Warr et al. |
| 2010/0183539 A1 | 7/2010 | Bernhardt |
| 2010/0215775 A1 | 8/2010 | Schmaus et al. |
| 2010/0287710 A1 | 11/2010 | Denutte et al. |
| 2010/0310644 A1 | 12/2010 | Liebmann |
| 2010/0322878 A1 | 12/2010 | Stella et al. |
| 2011/0008267 A1 | 1/2011 | Arkin et al. |
| 2011/0023266 A1 | 2/2011 | Gross et al. |
| 2011/0098209 A1 | 4/2011 | Smets et al. |
| 2011/0107524 A1 | 5/2011 | Chieffi et al. |
| 2011/0118691 A1 | 5/2011 | Nishitani |
| 2011/0139170 A1 | 6/2011 | Hippe et al. |
| 2011/0150815 A1 | 6/2011 | Woo et al. |
| 2011/0165107 A1 | 7/2011 | Derks et al. |
| 2011/0171155 A1 | 7/2011 | Federle |
| 2011/0177017 A1 | 7/2011 | Coffindaffer et al. |
| 2011/0232668 A1 | 9/2011 | Hoffmann et al. |
| 2011/0245126 A1 | 10/2011 | Tsaur et al. |
| 2011/0245134 A1 | 10/2011 | Smets |
| 2011/0245136 A1 | 10/2011 | Smets |
| 2011/0268778 A1 | 11/2011 | Dihora et al. |
| 2011/0269657 A1 | 11/2011 | Dihora et al. |
| 2011/0300095 A1 | 12/2011 | Dente et al. |
| 2011/0303766 A1 | 12/2011 | Smith |
| 2011/0305739 A1 | 12/2011 | Royce |
| 2011/0305778 A1 | 12/2011 | Caggioni et al. |
| 2011/0308555 A1 | 12/2011 | Smets et al. |
| 2011/0308556 A1 | 12/2011 | Smets et al. |
| 2011/0319790 A1 | 12/2011 | Kost et al. |
| 2012/0004328 A1 | 1/2012 | Huchel et al. |
| 2012/0009285 A1 | 1/2012 | Wei et al. |
| 2012/0014901 A1 | 1/2012 | Sunkel et al. |
| 2012/0031419 A1 | 2/2012 | Batt |
| 2012/0034173 A1 | 2/2012 | Batt |
| 2012/0052031 A1 | 3/2012 | Troccaz et al. |
| 2012/0100091 A1 | 4/2012 | Hata et al. |
| 2012/0100092 A1 | 4/2012 | Murray |
| 2012/0129924 A1 | 5/2012 | Park et al. |
| 2012/0219610 A1 | 8/2012 | Smith, III et al. |
| 2012/0230936 A1 | 9/2012 | Mikkelsen |
| 2012/0237469 A1 | 9/2012 | Dente et al. |
| 2012/0246851 A1 | 10/2012 | Smith, III et al. |
| 2012/0258150 A1 | 10/2012 | Rauckhorst et al. |
| 2012/0291911 A1 | 11/2012 | Smith |
| 2012/0309660 A1 | 12/2012 | Kawasoe |
| 2012/0316095 A1 | 12/2012 | Wei et al. |
| 2013/0029932 A1 | 1/2013 | Kachi et al. |
| 2013/0034515 A1 | 2/2013 | Stone et al. |
| 2013/0043145 A1 | 2/2013 | Smith, III et al. |
| 2013/0043146 A1 | 2/2013 | Smith, III et al. |
| 2013/0043147 A1 | 2/2013 | Smith, III et al. |
| 2013/0045285 A1 | 2/2013 | Stella et al. |
| 2013/0053295 A1 | 2/2013 | Kinoshita et al. |
| 2013/0053300 A1 | 2/2013 | Scheibel et al. |
| 2013/0089587 A1 | 4/2013 | Staudigel |
| 2013/0115173 A1 | 5/2013 | Trumbore et al. |
| 2013/0136713 A1 | 5/2013 | Terada et al. |
| 2013/0143784 A1 | 6/2013 | Rizk |
| 2013/0150338 A1 | 6/2013 | Ananthapadmanabhan |
| 2013/0156712 A1 | 6/2013 | Frantz |
| 2013/0189212 A1 | 7/2013 | Jawale et al. |
| 2013/0211952 A1 | 8/2013 | Sugaya |
| 2013/0216491 A1 | 8/2013 | Ogihara et al. |
| 2013/0243718 A1 | 9/2013 | Pasquet |
| 2013/0244922 A1 | 9/2013 | Bartelt |
| 2013/0266642 A1 | 10/2013 | Hollingshead et al. |
| 2013/0280192 A1 | 10/2013 | Carter et al. |
| 2013/0280202 A1 | 10/2013 | Stella et al. |
| 2013/0284195 A1 | 10/2013 | Murdock |
| 2013/0296289 A1 | 11/2013 | Hall et al. |
| 2013/0319463 A1 | 12/2013 | Policicchio |
| 2014/0037703 A1 | 2/2014 | Dihora et al. |
| 2014/0039066 A1 | 2/2014 | Grimadell et al. |
| 2014/0086893 A1 | 3/2014 | Gutmann et al. |
| 2014/0112879 A1 | 4/2014 | Molenda et al. |
| 2014/0127149 A1 | 5/2014 | Lepilleur |
| 2014/0131395 A1 | 5/2014 | Chang |
| 2014/0134125 A1 | 5/2014 | Dahl |
| 2014/0162979 A1 | 6/2014 | Palla-venkata |
| 2014/0171471 A1 | 6/2014 | Krueger |
| 2014/0186864 A1 | 7/2014 | Kato et al. |
| 2014/0201927 A1 | 7/2014 | Bianchetti et al. |
| 2014/0216495 A1 | 8/2014 | Bureiko |
| 2014/0221269 A1 | 8/2014 | Sobel et al. |
| 2014/0228268 A1 | 8/2014 | Fahl et al. |
| 2014/0237732 A1 | 8/2014 | Zuedel Fernandes et al. |
| 2014/0246515 A1 | 9/2014 | Nakajima |
| 2014/0308227 A1 | 10/2014 | Mabille |
| 2014/0309154 A1 | 10/2014 | Carter et al. |
| 2014/0335041 A1 | 11/2014 | Peffly et al. |
| 2014/0348884 A1 | 11/2014 | Hilvert et al. |
| 2014/0348886 A1 | 11/2014 | Johnson et al. |
| 2014/0349902 A1* | 11/2014 | Allef ................ A61Q 19/10 510/491 |
| 2015/0017152 A1 | 1/2015 | Potechin et al. |
| 2015/0021496 A1 | 1/2015 | Shabbir |
| 2015/0037273 A1 | 2/2015 | Wagner |
| 2015/0050231 A1 | 2/2015 | Murase |
| 2015/0071977 A1 | 3/2015 | Dihora |
| 2015/0093420 A1 | 4/2015 | Snyder |
| 2015/0093429 A1 | 4/2015 | Carter et al. |
| 2015/0098921 A1 | 4/2015 | Franzke et al. |
| 2015/0099684 A1 | 4/2015 | Boutique |
| 2015/0108163 A1 | 4/2015 | Smith et al. |
| 2015/0110728 A1* | 4/2015 | Jayaswal ............ A61Q 5/02 424/70.13 |

(56) References Cited

U.S. PATENT DOCUMENTS

| | | |
|---|---|---|
| 2015/0141310 A1 | 5/2015 | Smets et al. |
| 2015/0147286 A1 | 5/2015 | Barrera |
| 2015/0157548 A1 | 6/2015 | De Feij et al. |
| 2015/0218496 A1 | 8/2015 | Schmiedel et al. |
| 2015/0231045 A1 | 8/2015 | Krohn et al. |
| 2015/0262354 A1 | 9/2015 | Periaswamy |
| 2015/0297489 A1 | 10/2015 | Kleinen et al. |
| 2015/0299400 A1 | 10/2015 | Wagner et al. |
| 2015/0313818 A1 | 11/2015 | Stagg |
| 2015/0352027 A1 | 12/2015 | Thomas et al. |
| 2015/0359725 A1 | 12/2015 | Glenn, Jr. et al. |
| 2015/0359726 A1 | 12/2015 | Glenn, Jr. et al. |
| 2015/0359728 A1 | 12/2015 | Glenn, Jr. et al. |
| 2016/0008257 A1 | 1/2016 | Zhou et al. |
| 2016/0022566 A1 | 1/2016 | Figura |
| 2016/0089317 A1 | 3/2016 | Cetti et al. |
| 2016/0089318 A1 | 3/2016 | Cetti et al. |
| 2016/0089322 A1 | 3/2016 | Santos Nogueira et al. |
| 2016/0089462 A1 | 3/2016 | Frankenbach |
| 2016/0089464 A1 | 3/2016 | Frankenbach et al. |
| 2016/0089465 A1 | 3/2016 | Frankenbach et al. |
| 2016/0090555 A1 | 3/2016 | Frankenbach |
| 2016/0090556 A1 | 3/2016 | Frankenbach et al. |
| 2016/0090557 A1 | 3/2016 | Frankenbach et al. |
| 2016/0090558 A1 | 3/2016 | Frankenbach et al. |
| 2016/0092661 A1 | 3/2016 | Hollingshead et al. |
| 2016/0095804 A1 | 4/2016 | Xavier et al. |
| 2016/0113849 A1 | 4/2016 | Grimadell et al. |
| 2016/0128944 A1 | 5/2016 | Chawrai |
| 2016/0193125 A1 | 7/2016 | Jones et al. |
| 2016/0206522 A1 | 7/2016 | Ribaut et al. |
| 2016/0235643 A1 | 8/2016 | Mathonneau et al. |
| 2016/0250115 A1 | 9/2016 | Li et al. |
| 2016/0279048 A1 | 9/2016 | Jayaswal et al. |
| 2016/0287503 A1 | 10/2016 | Schroeder |
| 2016/0287509 A1 | 10/2016 | Peffly |
| 2016/0296656 A1 | 10/2016 | Scavone et al. |
| 2016/0303043 A1 | 10/2016 | Khoury |
| 2016/0306909 A1 | 10/2016 | Hollingshead et al. |
| 2016/0309871 A1 | 10/2016 | Torres Rivera et al. |
| 2016/0310369 A1 | 10/2016 | Thompson et al. |
| 2016/0310370 A1 | 10/2016 | Zhao et al. |
| 2016/0310371 A1 | 10/2016 | Zhao |
| 2016/0310375 A1 | 10/2016 | Torres Rivera |
| 2016/0310386 A1 | 10/2016 | Smith, III et al. |
| 2016/0310388 A1 | 10/2016 | Smith, III et al. |
| 2016/0310389 A1 | 10/2016 | Thompson et al. |
| 2016/0310390 A1 | 10/2016 | Smith, III et al. |
| 2016/0310391 A1 | 10/2016 | Smith, III et al. |
| 2016/0310393 A1 | 10/2016 | Chang et al. |
| 2016/0310402 A1 | 10/2016 | Zhao et al. |
| 2016/0317424 A1 | 11/2016 | Kadir et al. |
| 2016/0326458 A1 | 11/2016 | Smets et al. |
| 2016/0338929 A1 | 11/2016 | Zasloff |
| 2016/0354300 A1 | 12/2016 | Thompson et al. |
| 2017/0066579 A1 | 3/2017 | Zillges |
| 2017/0071837 A1 | 3/2017 | Schelges et al. |
| 2017/0101609 A1 | 4/2017 | Vargas |
| 2017/0110690 A1 | 4/2017 | Lamansky et al. |
| 2017/0110695 A1 | 4/2017 | Nishikawa et al. |
| 2017/0119917 A1 | 5/2017 | Frankenbach et al. |
| 2017/0137752 A1 | 5/2017 | Frankenbach et al. |
| 2017/0137753 A1 | 5/2017 | Frankenbach et al. |
| 2017/0165164 A1 | 6/2017 | Zhao et al. |
| 2017/0165165 A1 | 6/2017 | Zhao et al. |
| 2017/0209359 A1 | 7/2017 | Zhao et al. |
| 2017/0224607 A1 | 8/2017 | Li et al. |
| 2017/0239155 A1 | 8/2017 | Hartnett |
| 2017/0249407 A1 | 8/2017 | Cetti et al. |
| 2017/0249408 A1 | 8/2017 | Cetti et al. |
| 2017/0252273 A1 | 9/2017 | Renock et al. |
| 2017/0255725 A1 | 9/2017 | Frankenbach et al. |
| 2017/0278249 A1 | 9/2017 | Stofel |
| 2017/0283959 A1 | 10/2017 | Shellef |
| 2017/0304172 A1 | 10/2017 | Chang et al. |
| 2017/0304184 A1 | 10/2017 | Glenn, Jr. |
| 2017/0304185 A1 | 10/2017 | Glenn, Jr. et al. |
| 2017/0304186 A1 | 10/2017 | Glenn, Jr. |
| 2017/0333321 A1 | 11/2017 | Carnali |
| 2017/0333591 A9 | 11/2017 | Scavone et al. |
| 2017/0367963 A1 | 12/2017 | Kadir et al. |
| 2018/0004875 A1 | 1/2018 | Cetti et al. |
| 2018/0044097 A1 | 2/2018 | Zeik |
| 2018/0057451 A1 | 3/2018 | Owens et al. |
| 2018/0066210 A1 | 3/2018 | Frankenbach et al. |
| 2018/0098923 A1 | 4/2018 | Hutton, III |
| 2018/0110594 A1 | 4/2018 | Atkin |
| 2018/0110688 A1 | 4/2018 | Torres Rivera et al. |
| 2018/0110689 A1 | 4/2018 | Torres Rivera et al. |
| 2018/0110690 A1 | 4/2018 | Torres Rivera |
| 2018/0110691 A1 | 4/2018 | Torres Rivera et al. |
| 2018/0110692 A1 | 4/2018 | Torres Rivera et al. |
| 2018/0110693 A1 | 4/2018 | Renock et al. |
| 2018/0110694 A1 | 4/2018 | Renock et al. |
| 2018/0110695 A1 | 4/2018 | Thompson |
| 2018/0110696 A1 | 4/2018 | Johnson et al. |
| 2018/0110704 A1 | 4/2018 | Zhao et al. |
| 2018/0110707 A1 | 4/2018 | Zhao et al. |
| 2018/0110710 A1 | 4/2018 | Zhao et al. |
| 2018/0110714 A1 | 4/2018 | Glenn, Jr. et al. |
| 2018/0116937 A1 | 5/2018 | Park et al. |
| 2018/0116941 A1 | 5/2018 | Wang |
| 2018/0133133 A1 | 5/2018 | Kleinen et al. |
| 2018/0177708 A1 | 6/2018 | Lee et al. |
| 2018/0221266 A1 | 8/2018 | Zhao et al. |
| 2018/0256481 A1 | 9/2018 | Glenn, Jr. |
| 2018/0280270 A1 | 10/2018 | Rughani et al. |
| 2018/0311135 A1 | 11/2018 | Chang |
| 2018/0311136 A1 | 11/2018 | Chang |
| 2018/0318194 A1 | 11/2018 | Hoffmann et al. |
| 2018/0344611 A1 | 12/2018 | Zhao et al. |
| 2018/0344612 A1 | 12/2018 | Zhao et al. |
| 2018/0344613 A1 | 12/2018 | Zhao et al. |
| 2018/0344614 A1 | 12/2018 | Zhao et al. |
| 2018/0360713 A1 | 12/2018 | Jouy et al. |
| 2019/0105242 A1 | 4/2019 | Song |
| 2019/0105243 A1 | 4/2019 | Song |
| 2019/0105244 A1 | 4/2019 | Song |
| 2019/0105245 A1 | 4/2019 | Song |
| 2019/0105246 A1 | 4/2019 | Cochran |
| 2019/0105247 A1 | 4/2019 | Song |
| 2019/0117543 A1 | 4/2019 | Zhao |
| 2019/0117544 A1 | 4/2019 | Zhao |
| 2019/0117545 A1 | 4/2019 | Zhao |
| 2019/0125650 A1 | 5/2019 | Lee et al. |
| 2019/0142711 A1 | 5/2019 | Torres Rivera |
| 2019/0142800 A1 | 5/2019 | Ghosh et al. |
| 2019/0155975 A9 | 5/2019 | Cetti et al. |
| 2019/0167554 A1 | 6/2019 | Wankhade |
| 2019/0183777 A1 | 6/2019 | Gillis |
| 2019/0183778 A1 | 6/2019 | Glenn, Jr. |
| 2019/0192405 A1 | 6/2019 | Zhao |
| 2019/0240121 A1 | 8/2019 | Torres Rivera |
| 2019/0307298 A1 | 10/2019 | Zhao |
| 2019/0328647 A1 | 10/2019 | Chang et al. |
| 2019/0365619 A1 | 12/2019 | Ceballos et al. |
| 2019/0365633 A1 | 12/2019 | Glenn, Jr. |
| 2020/0000690 A1 | 1/2020 | Renock |
| 2020/0078284 A1 | 3/2020 | Botto et al. |
| 2020/0129402 A1 | 4/2020 | Jamadagni |
| 2020/0163846 A1 | 5/2020 | Song |
| 2020/0170894 A1 | 6/2020 | Park et al. |
| 2020/0197272 A1 | 6/2020 | Hertenstein et al. |
| 2020/0206110 A1 | 7/2020 | Hertenstein et al. |
| 2020/0237628 A1 | 7/2020 | Torres Rivera |
| 2021/0022986 A1 | 1/2021 | Glenn, Jr. |
| 2021/0093543 A1 | 4/2021 | Parikh et al. |
| 2021/0121385 A1 | 4/2021 | Muller et al. |
| 2021/0128444 A1 | 5/2021 | Muller et al. |
| 2021/0128447 A1 | 5/2021 | Galpin et al. |
| 2021/0212927 A1 | 7/2021 | Hutton, III et al. |
| 2021/0267853 A1 | 9/2021 | Johnson et al. |
| 2021/0275410 A1 | 9/2021 | Hutton, III |
| 2021/0353518 A1 | 11/2021 | Ballhaus et al. |

(56) References Cited

U.S. PATENT DOCUMENTS

| | | |
|---|---|---|
| 2021/0353522 A1 | 11/2021 | Ballhaus et al. |
| 2021/0401716 A1 | 12/2021 | Gogineni et al. |
| 2022/0062136 A1 | 3/2022 | Feng |
| 2022/0160606 A1 | 5/2022 | Renock |
| 2022/0378680 A1 | 12/2022 | Ballhaus et al. |
| 2022/0378684 A1 | 12/2022 | Cochran et al. |
| 2022/0395444 A1 | 12/2022 | Hutton, III |
| 2023/0053056 A1 | 2/2023 | Renock et al. |

FOREIGN PATENT DOCUMENTS

| | | |
|---|---|---|
| CA | 704195 A | 2/1965 |
| CA | 1248458 A | 1/1989 |
| CA | 2078375 A1 | 3/1994 |
| CN | 1263455 A | 8/2000 |
| CN | 1286612 A | 3/2001 |
| CN | 1545404 A | 11/2004 |
| CN | 1823929 A | 8/2006 |
| CN | 100534415 C | 9/2009 |
| CN | 101112349 B | 5/2011 |
| CN | 101690697 B | 10/2011 |
| CN | 101559034 B | 1/2013 |
| CN | 102895151 A | 1/2013 |
| CN | 102973437 A | 3/2013 |
| CN | 102697668 B | 8/2013 |
| CN | 103356408 A | 10/2013 |
| CN | 102697670 B | 7/2014 |
| CN | 104107401 A | 10/2014 |
| CN | 102851015 B | 12/2014 |
| CN | 105726393 A | 7/2016 |
| CN | 105769617 A | 7/2016 |
| CN | 106659664 A | 5/2017 |
| CN | 106750361 A | 5/2017 |
| CN | 107595657 A | 1/2018 |
| CN | 107595673 A | 1/2018 |
| CN | 107648096 A | 2/2018 |
| CN | 107737329 A | 2/2018 |
| CN | 107961212 A | 4/2018 |
| CN | 108186385 A | 6/2018 |
| CN | 108283583 A | 7/2018 |
| CN | 108451858 A | 8/2018 |
| CN | 110279591 A | 9/2019 |
| DE | 2145204 A1 | 3/1973 |
| DE | 3018456 A1 | 11/1981 |
| DE | 4315396 A1 | 11/1994 |
| DE | 102004012009 A1 | 9/2005 |
| DE | 202005009618 U1 | 9/2005 |
| DE | 102004023720 A1 | 12/2005 |
| DE | 102014225083 A | 10/2015 |
| DE | 102014225606 A1 | 10/2015 |
| DE | 102015204987 A1 | 9/2016 |
| EP | 0108517 A2 | 5/1984 |
| EP | 0574086 A2 | 12/1993 |
| EP | 0666358 A1 | 8/1995 |
| EP | 0674898 A2 | 10/1995 |
| EP | 1340485 A2 | 2/2003 |
| EP | 1346720 A2 | 9/2003 |
| EP | 067898 B2 | 3/2006 |
| EP | 1714678 A1 | 10/2006 |
| EP | 1842572 A2 | 10/2007 |
| EP | 2005939 A1 | 12/2008 |
| EP | 1970045 A3 | 9/2009 |
| EP | 2042216 B1 | 9/2015 |
| EP | 3121210 A1 | 1/2017 |
| EP | 3260171 A1 * | 12/2017 ............. A61K 8/368 |
| EP | 3622946 A1 | 3/2020 |
| ES | 2052450 B1 | 12/1994 |
| FR | 2669531 A1 | 5/1992 |
| FR | 2795955 A1 | 1/2001 |
| GB | 190110699 A | 8/1901 |
| GB | 191023922 A | 10/1911 |
| GB | 1347950 A | 2/1974 |
| GB | 2048229 | 12/1980 |
| GB | 2450727 A | 1/2009 |
| HU | 42318 | 7/1987 |
| JP | S56011009 A | 12/1981 |
| JP | S58113300 A | 7/1983 |
| JP | S58198412 A | 11/1983 |
| JP | AS60004598 A | 1/1985 |
| JP | S61236708 A | 10/1986 |
| JP | S62205200 A | 9/1987 |
| JP | S63501221 A | 5/1988 |
| JP | S63165308 A | 7/1988 |
| JP | H04364114 A | 12/1992 |
| JP | H06220495 A | 8/1994 |
| JP | H0753340 A | 2/1995 |
| JP | 07252134 A | 10/1995 |
| JP | H08310924 A | 11/1996 |
| JP | 09020618 A | 1/1997 |
| JP | 09030938 A | 2/1997 |
| JP | H09175961 A | 7/1997 |
| JP | H10017894 A | 1/1998 |
| JP | H11139944 A | 5/1999 |
| JP | 2964226 B2 | 10/1999 |
| JP | 2000178586 A | 6/2000 |
| JP | 3069802 B2 | 7/2000 |
| JP | 2001011492 A | 1/2001 |
| JP | 2001011497 A | 1/2001 |
| JP | 2001254099 A | 9/2001 |
| JP | 2001261529 A | 9/2001 |
| JP | 2003201217 A | 12/2001 |
| JP | 2002179552 A | 6/2002 |
| JP | 2002226889 A | 8/2002 |
| JP | 2002285191 A | 10/2002 |
| JP | 2002336337 A | 11/2002 |
| JP | 2003055699 A | 2/2003 |
| JP | 2003082398 A | 3/2003 |
| JP | 2003171688 A | 6/2003 |
| JP | 2003176497 A | 6/2003 |
| JP | 2003261413 A | 9/2003 |
| JP | 2003268398 A | 9/2003 |
| JP | 3480165 B2 | 12/2003 |
| JP | 2003342131 A | 12/2003 |
| JP | 3634988 B2 | 3/2005 |
| JP | 3634991 B2 | 3/2005 |
| JP | 3634996 B2 | 3/2005 |
| JP | 2005187359 A | 7/2005 |
| JP | 2005232113 A | 9/2005 |
| JP | 2006063044 A | 3/2006 |
| JP | 2006104149 A | 4/2006 |
| JP | 2006124312 A | 5/2006 |
| JP | 2006183039 A | 7/2006 |
| JP | 2006193549 A | 7/2006 |
| JP | 2006249092 A | 9/2006 |
| JP | 2006282565 A | 10/2006 |
| JP | 2007131687 A | 5/2007 |
| JP | 2007177047 A | 7/2007 |
| JP | 2007223935 A | 9/2007 |
| JP | 2008001626 A | 1/2008 |
| JP | 2008214292 A | 9/2008 |
| JP | 2009096778 A | 5/2009 |
| JP | 2009120559 A | 6/2009 |
| JP | 2009161866 A | 7/2009 |
| JP | 2011153167 A | 8/2011 |
| JP | 2011190221 A | 9/2011 |
| JP | 2011241353 A | 12/2011 |
| JP | 5041113 B2 | 7/2012 |
| JP | 2013010757 A | 1/2013 |
| JP | 2013091641 A | 5/2013 |
| JP | 2013151434 A | 8/2013 |
| JP | 2013155143 A | 8/2013 |
| JP | 2013193968 A | 9/2013 |
| JP | 2013216639 A | 10/2013 |
| JP | 6046394 B2 | 1/2014 |
| JP | 2014009177 A | 1/2014 |
| JP | 2014024875 A | 2/2014 |
| JP | 2014037383 A | 2/2014 |
| JP | 2014091723 A | 5/2014 |
| JP | 2014234350 A | 12/2014 |
| JP | 5667790 B2 | 2/2015 |
| JP | 2015034157 A | 2/2015 |
| JP | 2015101545 A | 6/2015 |
| JP | 2015129099 A | 7/2015 |
| JP | 2016013973 A | 1/2016 |

(56) References Cited

FOREIGN PATENT DOCUMENTS

| | | | |
|---|---|---|---|
| JP | 2016030722 A | 3/2016 | |
| JP | 2016088910 A | 5/2016 | |
| JP | 6184550 B1 | 8/2017 | |
| JP | 2018012673 A | 1/2018 | |
| KR | 100290589 B1 | 9/2001 | |
| KR | 100821846 B1 | 4/2008 | |
| KR | 1020080111280 A | 12/2008 | |
| KR | 20090095359 A | 9/2009 | |
| KR | 20100040180 A | 4/2010 | |
| KR | 20140060882 A | 5/2014 | |
| KR | 101494008 B1 | 2/2015 | |
| KR | 101503922 B1 | 3/2015 | |
| KR | 101532070 B1 | 7/2015 | |
| UA | 50333 U | 5/2010 | |
| WO | 8603679 A1 | 7/1986 | |
| WO | 9114759 A1 | 10/1991 | |
| WO | 91017237 A1 | 11/1991 | |
| WO | 9213520 A1 | 8/1992 | |
| WO | 199325650 A1 | 12/1993 | |
| WO | 9417783 A2 | 8/1994 | |
| WO | 9502389 A2 | 1/1995 | |
| WO | 9726854 A1 | 7/1997 | |
| WO | 9823258 A1 | 6/1998 | |
| WO | 9906010 A2 | 2/1999 | |
| WO | 9918928 A1 | 4/1999 | |
| WO | 9924004 A1 | 5/1999 | |
| WO | 9924013 A1 | 5/1999 | |
| WO | 9949837 A1 | 10/1999 | |
| WO | 9957233 A1 | 11/1999 | |
| WO | 0012553 A1 | 3/2000 | |
| WO | 0032601 | 6/2000 | |
| WO | 0119949 A1 | 3/2001 | |
| WO | 0142409 A1 | 6/2001 | |
| WO | 0148021 A1 | 7/2001 | |
| WO | WO2001076552 | * 10/2001 | ............... A61K 7/50 |
| WO | 2003051319 A1 | 6/2003 | |
| WO | 03096998 A1 | 11/2003 | |
| WO | 2004078901 A1 | 9/2004 | |
| WO | 2005023975 A1 | 3/2005 | |
| WO | 2008017540 A1 | 2/2008 | |
| WO | 2008128826 A1 | 10/2008 | |
| WO | 2008145582 A1 | 12/2008 | |
| WO | 2009016555 A2 | 2/2009 | |
| WO | 2009030594 A1 | 3/2009 | |
| WO | 2009035931 A1 | 4/2009 | |
| WO | 2010026009 A1 | 3/2010 | |
| WO | 2010052147 A2 | 5/2010 | |
| WO | 2012017091 A2 | 2/2012 | |
| WO | 2012052536 A2 | 4/2012 | |
| WO | 2012055587 A1 | 5/2012 | |
| WO | 2012055812 A1 | 5/2012 | |
| WO | 2012084970 A1 | 6/2012 | |
| WO | 2012127009 A1 | 9/2012 | |
| WO | 2012136651 A1 | 10/2012 | |
| WO | 2013010706 A2 | 1/2013 | |
| WO | 2013018805 A1 | 2/2013 | |
| WO | 2013119908 A1 | 8/2013 | |
| WO | 2014073245 A1 | 5/2014 | |
| WO | 2014073456 A1 | 5/2014 | |
| WO | 2014111667 A2 | 7/2014 | |
| WO | 2014111668 A2 | 7/2014 | |
| WO | 2014148245 A1 | 9/2014 | |
| WO | 2015067779 A1 | 5/2015 | |
| WO | 2015085376 A1 | 6/2015 | |
| WO | 2015122371 A1 | 8/2015 | |
| WO | 2015141787 A1 | 9/2015 | |
| WO | 2016049389 A1 | 3/2016 | |
| WO | 2016147196 A1 | 9/2016 | |
| WO | 2017052161 A1 | 3/2017 | |
| WO | 2017140798 A1 | 8/2017 | |
| WO | 2017140802 A1 | 8/2017 | |
| WO | 2017207685 A1 | 12/2017 | |
| WO | 2018023180 A1 | 2/2018 | |
| WO | 2018064511 A1 | 4/2018 | |
| WO | 2018109148 A1 | 6/2018 | |
| WO | 2019030458 A2 | 2/2019 | |
| WO | 2019074990 A1 | 4/2019 | |
| WO | 2019074992 A1 | 4/2019 | |
| WO | 2019200027 A1 | 10/2019 | |
| WO | 2020005309 A1 | 1/2020 | |
| WO | 2020030732 A1 | 2/2020 | |
| WO | 2021026572 A1 | 2/2021 | |
| WO | 2021099088 A1 | 5/2021 | |
| WO | 2021127318 A1 | 6/2021 | |
| WO | 2021144326 A1 | 7/2021 | |
| WO | 2021231510 A1 | 11/2021 | |

OTHER PUBLICATIONS

15686M PCT Search Report and Written Opinion for PCT/US2020/063222 dated Mar. 29, 2021, 06 pages.
Air Quality of the Iowa Department of Natural Resources. A Review of the Science and Technology of Odor Measurement, 2005, 51 pages (2005).
All Office Actions; U.S. Appl. No. 14/865,048, filed Sep. 25, 2015.
All Office Actions; U.S. Appl. No. 14/865,257, filed Sep. 25, 2015.
All Office Actions; U.S. Appl. No. 15/467,331, filed Mar. 23, 2017.
All Office Actions; U.S. Appl. No. 15/597,391, filed May 17, 2017.
All Office Actions; U.S. Appl. No. 15/597,376, filed May 17, 2017.
All Office Actions; U.S. Appl. No. 15/708,205, filed Sep. 19, 2017.
All Office Actions; U.S. Appl. No. 16/810,222, filed Mar. 5, 2020.
All Office Actions; U.S. Appl. No. 16/810,207, filed Mar. 4, 2020.
All Office Actions; U.S. Appl. No. 17/111,906, filed Dec. 4, 2020.
All Office Actions; U.S. Appl. No. 17/541,547, filed Dec. 3, 2021.
ASTM D3954-94, Reapproved 2010, vol. 15.04, Standard Test Method for Dropping Point of Waxes.
Brattoli et al. Odour Detection Methods: Offactometry and Chemical Sensors. Sensors (Basel), 2011; 11(5); 5290-5322 (2011).
Crepaldi, E.L., et al., Chemical, Structural, and Thermal Properties of Zn(II)—Cr(III) Layered Double Hydroxides Intercalated with Sulfated and Sulfonated Surfactants, Journal of Colloid and Interface Science, 2002, pp. 429-442, vol. 248.
Database GNPD [Online] Mintel;Mar. 28, 2018 (Mar. 28, 2018),anonymous: Dandruff Control Shampoo 11, XP055787038,Database accession No. 5556267abstract.
Database GNPD [Online] Mintel;Apr. 5, 2005 (Apr. 5, 2005),anonymous: "Anticaspa-Graso Anti-DandruffShampoo",XPC:I55787029,Database accession No. 351776paragraph [ingredients].
Database WPI; Week 201459; Thomson scientific, London, GB; AN 2014-P66521; XP002752638.
Grillet et al., "Polymer Gel Rheology and Adhesion", Rheology, 2012, pp. 59-80.
McGinley et al. American Association of Textile Chemists and Colorists, 2017, 17 pages, (2017).
McGinley et al. Performance Verification of Air Freshener Products and Other Odour Control Devices for Indoor Air Quality Malodours. Presented at the 8th Workshop on Odour and Emissions of Plastic Materials Universitat Kassel Institut for Wesrkstofftechnik Kassel, Germany, Mar. 27-28, 2006, 13 pages.
Morioka, H. et al. "Effects of Zinc on the New Preparation Method of Hydroxy Double Salts" Inorg. Chem. 1999, 38, 4211-6.
Sensory.,"A Review of the Science and Technology of Odor Measurement", Prepared for the Air Quality Bureau of the Iowa Department of Natural Resources, Dec. 30, 2005 51 pages.
Todd et al., Volatile Silicone Fluids for Cosmetics, Cosmetics and Toiletries, vol. 91, pp. 27-32 (Jan. 1976).
Unpublished U.S. Appl. No. 17/541,547, filed Dec. 15, 2021, to Stacy Renee Herteinstein et al.
"Anti-Dandruff Shampoo", Mintel Database, Record No. 752198, dated Aug. 2007 ; pp. 1-3.
"Dandruff Control Shampoo" , Mintel Database, Record No. 2300131, dated Jan. 2014; pp. 1-2.
"Foam & chemical contamination in waterways", Retrieved From https://www.epa.nsw.gov.au/-/media/epa/corporate-site/resources/epa/foam-chemical-contamination-in-waterway.pdf, Dec. 2015, 2 Pages.

(56) References Cited

OTHER PUBLICATIONS

"Natural Detangling Shampoo", Mintel Database, dated Sep. 13, 2017; 2 pages.
"Personal care solutions Guide", Solvay, Publication date: May 2018, 84 pages.
"Soda Shampoo", Mintel Database, dated Apr. 2015; pp. 1-4.
"Treatment Foam for Recurrent Scaling Conditions", Mintel Database, Aug. 2007; pp. 1-2.
Acne Foaming Cleanser, Database accession No. 4172863, Jul. 29, 2016, 3 pages.
Anonymous: "Merquat Polyquaternium 47 Series, Water Soluble Polymers for Personal Care", Jul. 30, 2017, URL: https://www.in-cosmetics.com/_novadocuments/2729, retrieved on Dec. 21, 2018; 1 page.
Anonymous: "Anti-Dandruff Scalp Care Shampoo", Mintel, Database accession No. 301924, Sep. 16, 2004, 2 pages.
Anonymous: "Naturally Derived Body Wash", Database GNPD [Online] Mintel; Feb. 15, 2021, 2 pages.
Anonymous: "Peptide Shampoo", Database GNPD [Online] Mintel; Dec. 14, 2015, 3 pages.
Anonymous: "Replenishing Moisture Shampoo", Database GNPD [Online] Mintel, Mar. 10, 2015br.
Anonymous: "Shampoo", Database GNPD [Online] Mintel, Jan. 26, 2021, 3 pages.
Anonymous: "Shampooing au Phytolait d'abricot—Formule N°102-MP06-MI3-AA03", Internet Citation, Feb. 19, 2005, Retrieved from the Internet:URL: http://web.archive.org/web/20050219040350/www.albanmuller.com/francais/catalogue/formules/formul10.asp, 1 page.
Carbopol Aqua SF-1 Polymer Technical Data Sheet, TDS-294, dated Dec. 2000 ; pp. 1-9.
Christensen et al., "Experimental Determination of Bubble Size Distribution in a Water Column by Interferometric Particle Imaging and Telecentric Direct Image Method", Student Report, Aalborg University; dated Jun. 3, 2014; 123 pages.
D'Souza et al., Shampoo and Conditioners: What a Dermatologist Should Know? Indian J Dermatol, dated May-Jun. 2015; pp. 60(3), 248-254 (2015).
Database GNPD [Online] Mintel; Jan. 6, 2020 (Jan. 6, 2020), anonymous: 11 Shampoo 11, 3 pages.
Datasheet: Empigen Total Active TC/U, Datasheet, dated Jan. 31, 2017 (Innospec) ; 2 pages.
Dehyquart Guar: Published dated Nov. 2010 ; pp. 1-34.
Fevola, Michael J. "Guar Hydroxypropyltrimonium Chloride." Cosmetics and toiletries; vol. 127.1; Jan. 2012 ; pp. 16-21.
Hair Care/Conditioning Polymers Differentiation, Anonymous, Feb. 1, 2017, URL: http://www.biochim.it./assets/site/media/allegati/cosmetica/hair-care/tab-merquat-hair-care.pdf, retrieved on Dec. 20, 2018; p. 1.
Happi: "Sulfate-Free Surfactants Conditioning Shampoo", Retrieved from the Internet: URL:https://www.happi.com/contents/view_formulary/2009-10-01/sulfate-free-surfactants-conditioning-shampoo/, XP002804301, Jan. 10, 2019, 1 page.
Inspection certificate for Hostapon® CCG, Clariant Ibérica Production, S.A., May 6, 2019; p. 1-2.
Medvedev, Diffusion Coefficients in Multicomponent Mixtures, PhD Thesis from Technical University of Denmark, dated 2005, 181 pages.
Mintel GNPD Base, Bright Blonde Shampoo Record No. 3412889 Feb. 29, 2016 ; 2 pages.
Mintel GNPD Base, Mineral Conquer Blonde Silver Shampoo Record No. 3953107 Apr. 30, 2016; 2 pages.
Mintel GNPD Base, Royal Treatment Collection, Record No. 1946223 dated Dec. 31, 2011, 3 pages.
Musazzi, "Emulsion versus nonoemulsion: how much is the formulative shift critical for a cosmetic product?" (Drug Deliv. and Trans. Res. (2018) 8: pp. 414-421 (Year: 2018).
Natural oils: why specific carbon chains are chosen for certain surfactant properties, Chemlink, URL Link: https://www.chemlink.co.uk/natural-oils-why-specific-carbon-chains-are-chosen-for-certain-surfactant-properties/a (Year: 2022), 4 pgs.
Naturally Rich Moisturizing Shampoo, Database accession No. 6421011, Mar. 27, 2019, 3 pages.
Noritomi H. Formation and Solubilization Property of Water-in-Oil Microemulsions of Alkyl Glucoisdes. Advances in Nanoparticles, 2013, 2, 366-371 (Year: 2013).
Parchem fine & specialty chemicals. MIPA-laureth sulfate supplier distributor—CAS 83016-76-6; dated 2021; pp. 1-7.
Perm Inc, , Diffusion Coefficient: Measurement Techiques, https://perminc.com/resources/fundamentals-of-fluid-flow-in-porous-media/chapter-3-molecular-diffusion/diffusion-coefficient/measurement-techniques, dated Oct. 2020; p. 1-4.
Polyquaternium: "Final Report on the Safety Assessment of the Polyquaternium-10", Journal of the American College of Toxicology, Jan. 1, 1988, URL: http://www.beauty-review.nl/wp-content/uploads/2015/02/Final-Report-on-the Safety-Assessment-of-Polyquaternium-10.pdf, retrieved on Dec. 20, 2018; 9 pages.
Practical Modern Hair Science, Published 2012; 43 pages.
Product Bulletin, Amphosol® CG, Cocamidopropyl Betaine, Stepan Company, Jun. 2011; 1-2 pages.
Product Data Record Tego®Betain F KB 5, dated Jul. 1, 2015, 4 pages.
Product Data Sheet for Chemoryl™LS Surfactant, Sodium Lauroyl Sarcosinate, Lubrizol Advanced Materials, Inc., Mar. 24, 2020; 1-2 pages.
Product Data Sheet, Eversoft™ UCS-40S, Disodium Cocoyl Glutamate (Sodium Cocoyl Glutamate*), Sino Lion USA, Jul. 2018; 2 pages.
Product Fact Sheet—Hostapon® CCG, mild anionic surfactant for the cosmetic industry, Clariant International Ltd., Aug. 2014 ; 1-3 pages.
Product Fact Sheet, Hostapon® CGN, Mild anionic surfactant for the cosmetic industry, Clariant International Ltd., Jan. 2016; 1-2 pages.
Rajendran A. et al: "Study on the Analysis of Trace Elements in Aloe veraand Its Biological Importance Study on the Analysis of Trace Elements in Aloe vera and Its Biological Importance", Journal of Applied Sciences Research,Jan. 1, 2007 (Jan. 1, 2007), pp. 1476-1478.
Robinson et al., Final Report of the Amended Safety Assessment of Sodium Laureth Sulfate and Related Salts of SulfatedEthoxylated Alcohols, International Journal of Toxicology 29 (Supplement 3); dated 2010; pp. 151S-161S.
S. Herrwerth et al.: "Highly Concentrated Cocamidopropyl Betaine—The Latest Developments for Improved Sustainability and Enhanced Skin Care", Tenside, Surfactants, Detergents, vol. 45, No. 6, dated Nov. 1, 2008, pp. 304-308, p. 305—left-hand column; 3 pages.
Safety assessment of amino acid alkyl amides used in cosmetics , dated Sep. 20, 2013, 46 pages.
Schaefer, Katie, "Eco-friendly, Non-flammable Liquified Gas Propellant", https://www.cosmeticsandtoiletries.com/formulating/function/aids/138418589.html#close-olyticsmodal. Published Jan. 30, 2012; 1-2 pages.
Shampoo C, Database accession No. 1632217, Sep. 29, 2011, 3 pages.
Softazoline CL-R, Kawaken Singapore PTE Ltd. Website printout from http://kawaken.com.sg/softazoline-ch-r//a, accessed on Nov. 30, 2022.
UL Prospector® Product Data Sheet, Plantacare® 818 UP, C8-16 fatty alcohol glucoside, BASF, dated May 21, 2015; 1-3 pages.
Unhale Shrikrushna Subhash et al: Formulation and Development of Sulphate Free Shampoo About an Updates andGuidelines of Corona Virus View project health and beauty science View project Rohit Bhavsar Reliance Industries Limited; International Journal for Research inApplied Science & Engineering Technology, Apr. 1, 2020 (Apr. 1, 2020), DOI: 10.22214, 14 pages.
"Deep Image Matting", Ning Xu et al., Beckman Institute for Advanced Science and Technology, University of Illinois at Urbana—Champaign, Adobe Research, dated Mar. 10, 2017; 10 pages.
"Comparative Study on the Chemical constituents of Aloe Vera and Aloe Kula in China ", Zhang Xiaohua et al., Flavor Cosmetics, No. 63, dated Dec. 31, 2000, pp. 7-11.

(56) References Cited

OTHER PUBLICATIONS

PubChem CID 3033856 for decyl glucoside. downloaded Jun. 22, 2023, 32 pages. (Year: 2023).

"Jaguar® Optima", Solvay, site: www.solvay.com, year 2023, 1 page.

Cafasso, "What's the proper order to use shampoo and conditioner while bathing", Healthline, Retrieved from Internet: https://www.healthline.com/health/beauty-skin-care/shampoo-or-conditioner-first, dated Jul. 13, 2020, 2 pages.

Duis et al., "Environmental fate and effects of water-soluble synthetic organic polymers used in cosmetic products", Enviromental Sciences Europe, 33:21, Year 2021; 20 pages.

Matsouka et al., "Vesicle formation of disodium lauryl sulfosuccinate", Journal of Molecular Liquids, 348, 118422, Nov. 1, 2021, 7 pages.

Ramachandra et al., "Processing of Aloe Vera Leaf Gel: A Review", American Journal of Agricultural and Biological Sciences 3 (2), year 2008, pp. 502-510.

Shampoo, ID# 6148479, Mintel GNPD [online], URL: http://www.gnpd.com, Nov. 2018, 4 pages.

Yang et al., "Synthesis and foaming performance of Lauramidopropyl Betaine Derivate Surfactants", Materials Science Forum, vol. 953, Jan. 9, 2019, 1 page.

All Office Actions; U.S. Appl. No. 18/484,074, filed Oct. 10, 2023.

U.S. Appl. No. 18/484,074, filed Oct. 10, 2023 to Stacy Renee Hertenstein et al.

Anonymous, "Medicated Cleanser", Nioxin Research Laboratories, Mintel GNPD [online], ID: 1060983, URL: http://www.gnpd.com, dated Feb. 2009, 4 pages.

Anonymous, "Healing + Anti-Breakage Shampoo", ID# 3383875, Mintel GNPD, URL: http://www.gnpd.com, dated Aug. 2015, 3 pages.

Anonymous, "Shampoo", ID# 1743027, Mintel GNPD, URL: http://www.gnpd.com, dated Mar. 2012, 3 pages.

Technical Information: TEGO® Betain F KB 5 / TEGO® Betain F KM 1; Mild amphoteric surfactants: www.evonik.com/personal-care; Jul. 2010; 2 pages; Product Specification; 5 pages.

* cited by examiner

SULFATE FREE COMPOSITION WITH ENHANCED DEPOSITION OF SCALP ACTIVE

FIELD OF THE INVENTION

The present invention is directed to a personal care composition containing sulfate free surfactants in combination with a cationic polymer and an alkali swellable emulsion polymer. Upon dilution, these polymers will complex and deliver to scalp and hair antidandruff active deposition benefits with resulting antidandruff efficacy.

BACKGROUND OF THE INVENTION

Anti-dandruff shampoos have been widely used to treat dandruff and clean hair and scalp with predominately sulfated surfactants. These sulfated surfactants, although clean effectively, may cause irritation to consumers with sensitive scalp skin. Therefore, less irritating surfactants such as sulfate free surfactants, may be a better alternative for antidandruff shampoo formulation. In general, anti-dandruff shampoos are formulated with anti-dandruff agents in combination with surfactants and aqueous systems that are intended to deposit the anti-dandruff agents on the scalp. The anti-dandruff agents can be insoluble particulates such as zinc pyrithione, sulfur, and/or surfactant soluble substances such as climbazole or piroctone olamine. An important aspect of the anti-dandruff shampoos is its ability to enable enough deposition of the anti-dandruff agent on the scalp to effectively kill and inhibit growth of the fungus *Malassezia*. Within a sulfate free shampoo system, it has been challenging to deliver anti-dandruff agents where it can deposit on scalp more than 1-2% of the quantity of the agent that is present in the product, while the remaining 98-99% of the antidandruff active in the formulas is rinsed away. Current high efficacy antidandruff shampoo formulations contain both active zinc pyrithione and potentiator zinc carbonate, hereafter referred to as potentiated zinc pyrithione or potentiated ZPT. The potentiator enables zinc stability and very effective/efficient fungal efficacy from these formulation types. Therefore, formulations considered non potentiators, not containing zinc carbonate, require much more active deposition on scalp and hair to match the efficacy of potentiated zinc pyrithione. The formation of coacervate via cationic polymer interaction with anionic surfactant upon dilution has been the classic way to deposit insoluble antidandruff actives to the hair and scalp. Within a sulfate free shampoo, it has been difficult to generate a coacervate which would be adhesive enough to entrap antidandruff active and deposit effectively to hair and scalp. Therefore, the need for a more effective deposition mechanism of the antidandruff active from a less harsh sulfate free surfactant containing shampoo is required.

The present invention has surprisingly found that shampoos comprised of sulfate free surfactants with cationic polymer and an alkali swellable emulsion polymer can deliver increased quantities of antidandruff zinc pyrithione active to the scalp that results in highly effective antifungal scalp efficacy when compared to sulfated antidandruff shampoo with potentiated zinc pyrithione. In addition, such compositions have also been found to provide consumer perceived antidandruff health benefits.

SUMMARY OF THE INVENTION

The present invention is directed to a personal care composition comprising from about 15% to about 22% of one or more sulfate free surfactants; from about 0.1% to about 10% of one or more scalp active; from about 0.1% to about 1.2% of a cationic polymers having a molecular weight in the range of 50,000 to less than or equal to 1.8 million and a charge density of about 0.5 to about 1.7 meq/g, from about 0.1% to about 1.2% of a rheology modifier and having a pH of about 5 to about 7 and having a viscosity of >about 5000 cps.

DETAILED DESCRIPTION OF EMBODIMENTS OF THE INVENTION

All percentages and ratios used herein are by weight of the total composition, unless otherwise designated. All measurements are understood to be made at ambient conditions, where "ambient conditions" means conditions at about 25° C., under about one atmosphere of pressure, and at about 50% relative humidity, unless otherwise designated. All numeric ranges are inclusive of narrower ranges; delineated upper and lower range limits are combinable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

"Apply" or "application," as used in reference to a composition, means to apply or spread the compositions of the present invention onto keratinous tissue such as the hair.

"Dermatologically acceptable" means that the compositions or components described are suitable for use in contact with human skin tissue without undue toxicity, incompatibility, instability, allergic response, and the like.

"Safe and effective amount" means an amount of a compound or composition sufficient to significantly induce a positive benefit.

While the specification concludes with claims particularly pointing out and distinctly claiming the invention, it is believed that the present invention will be better understood from the following description.

As used herein, the term "fluid" includes liquids and gels.

As used herein, the articles including "a" and "an" when used in a claim, are understood to mean one or more of what is claimed or described.

As used herein, "comprising" means that other steps and other ingredients which do not affect the end result can be added. This term encompasses the terms "consisting of" and "consisting essentially of".

As used herein, "mixtures" is meant to include a simple combination of materials and any compounds that may result from their combination.

As used herein, "molecular weight" or "Molecular weight" refers to the weight average molecular weight unless otherwise stated. Molecular weight is measured using industry standard method, gel permeation chromatography ("GPC").

Where amount ranges are given, these are to be understood as being the total amount of said ingredient in the composition, or where more than one species fall within the scope of the ingredient definition, the total amount of all ingredients fitting that definition, in the composition.

For example, if the composition comprises from 1% to 5% fatty alcohol, then a composition comprising 2% stearyl alcohol and 1% cetyl alcohol and no other fatty alcohol, would fall within this scope.

The amount of each particular ingredient or mixtures thereof described hereinafter can account for up to 100% (or 100%) of the total amount of the ingredient(s) in the personal care composition.

As used herein, "personal care compositions" includes products such as shampoos, shower gels, liquid hand cleansers, hair colorants, facial cleansers, and other surfactant-based liquid compositions.

As used herein, the terms "include," "includes," and "including," are meant to be non-limiting and are understood to mean "comprise," "comprises," and "comprising," respectively.

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Scalp Active

The present invention may comprise a scalp active, which may be an anti-dandruff active material. The anti-dandruff active may be selected from the group consisting of: pyridinethione salts; zinc carbonate; azoles, such as ketoconazole, econazole, and elubiol; selenium sulphide; particulate sulfur; keratolytic agents such as salicylic acid; and mixtures thereof. The anti-dandruff particulate may be a pyridinethione salt. Such anti-dandruff particulate should be physically and chemically compatible with the components of the composition, and should not otherwise unduly impair product stability, aesthetics or performance The concentration of the scalp active may be in the range of from about 0.1% to about 10%; from about 2% to about 5%; and from about 1% to about 2%.

Pyridinethione particulates are suitable particulate anti-dandruff actives for use in composition of the present invention. The anti-dandruff active may be a 1-hydroxy-2-pyridinethione salt and is in particulate form. The concentration of pyridinethione anti-dandruff particulate may range from about 0.01% to about 5%, by weight of the composition, or from about 0.1% to about 3%, or from about 1% to about 2%. The pyridinethione salts may be those formed from heavy metals such as zinc, tin, cadmium, magnesium, aluminium and zirconium, generally zinc, typically the zinc salt of 1-hydroxy-2-pyridinethione (known as "zinc pyridinethione" or "ZPT"; zinc pyrithione), commonly 1-hydroxy-2-pyridinethione salts in platelet particle form. The 1-hydroxy-2-pyridinethione salts may be in platelet particle form having an average particle size of up to about 20 microns, or up to about 5 microns, or up to about 2.5 microns. Salts formed from other cations, such as sodium, may also be suitable. Pyridinethione anti-dandruff actives are described, for example, in U.S. Pat. Nos. 2,809,971; 3,236,733; 3,753, 196; 3,761,418; 4,345,080; 4,323,683; 4,379,753; and 4,470,982.

In addition to the anti-dandruff active selected from polyvalent metal salts of pyrithione, the composition may further comprise one or more anti-fungal and/or anti-microbial actives. The anti-microbial active may be selected from the group consisting of: coal tar, sulfur, charcoal, copper pyrithione, whitfield's ointment, castellani's paint, aluminium chloride, gentian violet, hydroxyl pyridine and wherein the hydroxyl pyridine may be piroctone olamine, octopirox (piroctone olamine), ciclopirox olamine, rilopirox, MEA-Hydroxyoctyloxypyridinone; strobilurins such as azoxystrobin and metal chelators such as 1,10-phenanthroline, undecylenic acid and its metal salts, potassium permanganate, selenium sulphide, sodium thiosulfate, propylene glycol, oil of bitter orange, urea preparations, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone, and azoles, and mixtures thereof. The anti-microbial may be selected from the group consisting of: itraconazole, ketoconazole, selenium sulphide, coal tar, and mixtures thereof.

The azole anti-microbials may be an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of: terconazole, itraconazole, and mixtures thereof. When present in the composition, the azole anti-microbial active is included in an amount of from about 0.01% to about 5%, or from about 0.1% to about 3%, or from about 0.3% to about 2%, by total weight of the composition. The azole anti-microbial active may be ketoconazole. The sole anti-microbial active may be ketoconazole.

The present invention may also comprise a combination of anti-microbial actives. The combination of anti-microbial active may be selected from the group of combinations consisting of: octopirox and zinc pyrithione, pine tar and sulfur, salicylic acid and zinc pyrithione, salicylic acid and elubiol, zinc pyrithione and elubiol, zinc pyrithione and climbasole, octopirox and climbasole, salicylic acid and octopirox, and mixtures thereof.

The composition may comprise an effective amount of a zinc-containing layered material. The composition may comprise from about 0.001% to about 10%, or from about 0.01% to about 7%, or from about 0.1% to about 5% of a zinc-containing layered material, by total weight of the composition.

Zinc-containing layered materials may be those with crystal growth primarily occurring in two dimensions. It is conventional to describe layer structures as not only those in which all the atoms are incorporated in well-defined layers, but also those in which there are ions or molecules between the layers, called gallery ions (A.F. Wells "Structural Inorganic Chemistry" Clarendon Press, 1975). Zinc-containing layered materials (ZLMs) may have zinc incorporated in the layers and/or be components of the gallery ions. The following classes of ZLMs represent relatively common examples of the general category and are not intended to be limiting as to the broader scope of materials which fit this definition.

Many ZLMs occur naturally as minerals. The ZLM may be selected from the group consisting of: hydrozincite (zinc carbonate hydroxide), basic zinc carbonate, aurichalcite (zinc copper carbonate hydroxide), rosasite (copper zinc carbonate hydroxide), and mixtures thereof. Related minerals that are zinc-containing may also be included in the composition. Natural ZLMs can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLMs, which are often, but not always, synthetic, is layered double hydroxides. The ZLM may be a layered double hydroxide conforming to the formula $[M^{2+}_{1-x}M^{3+}_x(OH)_2]^{x+}A^{m-}_{x/m} \cdot nH_2O$ wherein some or all of the divalent ions ($M^{2+}$) are zinc ions (Crepaldi, E L, Pava, P C, Tronto, J, Valim, J B *J. Colloid Interfac. Sci.* 2002, 248, 429-42).

Yet another class of ZLMs can be prepared called hydroxy double salts (Morioka, H., Tagaya, H., Karasu, M, Kadokawa, J, Chiba, K *Inorg. Chem.* 1999, 38, 4211-6). The ZLM may be a hydroxy double salt conforming to the formula $[M^{2+}_{1-x}M^{2+}_{1-x}(OH)_{3(1-y)}]^+A^{n-}_{(1=3y)/n} \cdot nH_2O$ where the two metal ions ($M^{2+}$) may be the same or different. If they are the same and represented by zinc, the formula simplifies to $[Zn_{1+x}(OH)_2]^{2x+}2 \times A^- \cdot nH_2O$. This latter formula represents (where x=0.4) materials such as zinc hydroxychloride and zinc hydroxynitrate. THe ZLM may be zinc hydroxychloride and/or zinc hydroxynitrate. These are related to hydrozincite as well wherein a divalent anion replace the monovalent anion. These materials can also be formed in situ in a composition or in or during a production process.

The composition may comprise basic zinc carbonate. Commercially available sources of basic zinc carbonate include Zinc Carbonate Basic (Cater Chemicals: Bensenville, IL, USA), Zinc Carbonate (Shepherd Chemicals: Norwood, OH, USA), Zinc Carbonate (CPS Union Corp.: New York, New York, USA), Zinc Carbonate (Elementis Pigments: Durham, UK), and Zinc Carbonate AC (Bruggemann Chemical: Newtown Square, PA, USA). Basic zinc carbonate, which also may be referred to commercially as "Zinc Carbonate" or "Zinc Carbonate Basic" or "Zinc Hydroxy Carbonate", is a synthetic version consisting of materials similar to naturally occurring hydrozincite. The idealized stoichiometry is represented by $Zn_5(OH)_6(CO_3)_2$ but the actual stoichiometric ratios can vary slightly and other impurities may be incorporated in the crystal lattice.

The composition may contain a zinc-containing layered material and a pyrithione or polyvalent metal salt of pyrithione, the ratio of zinc-containing layered material to pyrithione or a polyvalent metal salt of pyrithione is from about 5:100 to about 10:1, or from about 2:10 to about 5:1, or from about 1:2 to about 3:1.

A. Detersive Surfactant

The cleansing compositions described herein can include one or more surfactants in the surfactant system. The one or more surfactants can be substantially free of sulfate-based surfactants. As can be appreciated, surfactants provide a cleaning benefit to soiled articles such as hair, skin, and hair follicles by facilitating the removal of oil and other soils. Surfactants generally facilitate such cleaning due to their amphiphilic nature which allows for the surfactants to break up, and form micelles around, oil and other soils which can then be rinsed out, thereby removing them from the soiled article. Suitable surfactants for a cleansing composition can include anionic moieties to allow for the formation of a coacervate with a cationic polymer. The surfactant can be selected from anionic surfactants, amphoteric surfactants, zwitterionic surfactants, non-ionic surfactants, and combinations thereof.

Cleansing compositions typically employ sulfate-based surfactant systems (such as, but not limited to, sodium lauryl sulfate) because of their effectiveness in lather production, stability, clarity and cleansing. The cleansing compositions described herein are substantially free of sulfate-based surfactants. "Substantially free" of sulfate based surfactants as used herein means from about 0 wt % to about 3 wt %, alternatively from about 0 wt % to about 2 wt %, alternatively from about 0 wt % to about 1 wt %, alternatively from about 0 wt % to about 0.5 wt %, alternatively from about 0 wt % to about 0.25 wt %, alternatively from about 0 wt % to about 0.1 wt %, alternatively from about 0 wt % to about 0.05 wt %, alternatively from about 0 wt % to about 0.01 wt %, alternatively from about 0 wt % to about 0.001 wt %, and/or alternatively free of sulfates. As used herein, "free of" means 0 wt %.

Additionally, the surfactant systems described herein have from about 0 wt % to about 1 wt % of inorganic salts.

Suitable surfactants that are substantially free of sulfates can include sodium, ammonium or potassium salts of isethionates; sodium, ammonium or potassium salts of sulfonates; sodium, ammonium or potassium salts of ether sulfonates; sodium, ammonium or potassium salts of sulfosuccinates; sodium, ammonium or potassium salts of sulfoacetates; sodium, ammonium or potassium salts of glycinates; sodium, ammonium or potassium salts of sarcosinates; sodium, ammonium or potassium salts of glutamates; sodium, ammonium or potassium salts of alaninates; sodium, ammonium or potassium salts of carboxylates; sodium, ammonium or potassium salts of taurates; sodium, ammonium or potassium salts of phosphate esters; and combinations thereof. The concentration of the surfactant in the composition should be sufficient to provide the desired cleaning and lather performance. The cleansing composition can comprise a total surfactant level of from about 6% to about 50%, from about 5% to about 35%, a total surfactant level of from about 10% to about 50%, by weight, from about 15% to about 45%, from about 15% to about 22%; from about 16% to about 20%; from about 17% to about 20%; by weight, from about 20% to about 40%, by weight, from about 22% to about 35%, and/or from about 25% to about 30%.

The surfactant system can include one or more amino acid based anionic surfactants. Non-limiting examples of amino acid based anionic surfactants can include sodium, ammonium or potassium salts of acyl glycinates; sodium, ammonium or potassium salts of acyl sarcosinates; sodium, ammonium or potassium salts of acyl glutamates; sodium, ammonium or potassium salts of acyl alaninates and combinations thereof.

The amino acid based anionic surfactant can be a glutamate, for instance an acyl glutamate. The composition can comprise an acyl glutamate level from about 2% to about 22%, by weight, from about 3% to about 19%, by weight, 4% to about 17%, by weight, and/or from about 5% to about 15%, by weight.

Non-limiting examples of acyl glutamates can be selected from the group consisting of sodium cocoyl glutamate, disodium cocoyl glutamate, ammonium cocoyl glutamate, diammonium cocoyl glutamate, sodium lauroyl glutamate, disodium lauroyl glutamate, sodium cocoyl hydrolyzed wheat protein glutamate, disodium cocoyl hydrolyzed wheat protein glutamate, potassium cocoyl glutamate, dipotassium cocoyl glutamate, potassium lauroyl glutamate, dipotassium lauroyl glutamate, potassium cocoyl hydrolyzed wheat protein glutamate, dipotassium cocoyl hydrolyzed wheat protein glutamate, sodium capryloyl glutamate, disodium capryloyl glutamate, potassium capryloyl glutamate, dipotassium capryloyl glutamate, sodium undecylenoyl glutamate, disodium undecylenoyl glutamate, potassium undecylenoyl glutamate, dipotassium undecylenoyl glutamate, disodium hydrogenated tallow glutamate, sodium stearoyl glutamate, disodium stearoyl glutamate, potassium stearoyl glutamate, dipotassium stearoyl glutamate, sodium myristoyl glutamate, disodium myristoyl glutamate, potassium myristoyl glutamate, dipotassium myristoyl glutamate, sodium cocoyl/hydrogenated tallow glutamate, sodium cocoyl/palmoyl/sunfloweroyl glutamate, sodium hydrogenated tallowoyl Glutamate, sodium olivoyl glutamate, disodium olivoyl glutamate, sodium palmoyl glutamate, disodium palmoyl Glutamate, TEA-cocoyl glutamate, TEA-hydrogenated tallowoyl glutamate, TEA-lauroyl glutamate, and mixtures thereof.

The amino acid based anionic surfactant can be an alaninate, for instance an acyl alaninate. Non-limiting example of acyl alaninates can include sodium cocoyl alaninate, sodium lauroyl alaninate, sodium N-dodecanoyl-1-alaninate and combination thereof. The composition can comprise an acyl alaninate level from about 2% to about 20%, by weight, from about 7% to about 15%, by weight, and/or from about 8% to about 12%, by weight.

The amino acid based anionic surfactant can be a sarcosinate, for instance an acyl sarcosinate. Non-limiting examples of sarcosinates can be selected from the group consisting of sodium lauroyl sarcosinate, sodium cocoyl sarcosinate, sodium myristoyl sarcosinate, TEA-cocoyl sarcosinate, ammonium cocoyl sarcosinate, ammonium lauroyl sarcosinate, dimer dilinoleyl bis-lauroylglutamate/lauroyl-sarcosinate, disodium lauroamphodiacetate lauroyl sarcosinate, isopropyl lauroyl sarcosinate, potassium cocoyl sarcosinate, potassium lauroyl sarcosinate, sodium cocoyl sarcosinate, sodium lauroyl sarcosinate, sodium myristoyl sarcosinate, sodium oleoyl sarcosinate, sodium palmitoyl sarcosinate, TEA-cocoyl sarcosinate, TEA-lauroyl sarcosinate, TEA-oleoyl sarcosinate, TEA-palm kernel sarcosinate, and combinations thereof.

The amino acid based anionic surfactant can be a glycinate for instance an acyl glycinate. Non-limiting example of acyl glycinates can include sodium cocoyl glycinate, sodium lauroyl glycinate and combination thereof.

The composition can contain additional anionic surfactants selected from the group consisting of sulfosuccinates, isethionates, sulfonates, sulfoacetates, glucose carboxylates, alkyl ether carboxylates, acyl taurates, and mixture thereof.

Non-limiting examples of sulfosuccinate surfactants can include disodium N-octadecyl sulfosuccinate, disodium lauryl sulfosuccinate, diammonium lauryl sulfosuccinate, sodium lauryl sulfosuccinate, disodium laureth sulfosuccinate, tetrasodium N-(1,2-dicarboxyethyl)-N-octadecyl sulfosuccinnate, diamyl ester of sodium sulfosuccinic acid, dihexyl ester of sodium sulfosuccinic acid, dioctyl esters of sodium sulfosuccinic acid, and combinations thereof. The composition can comprise a sulfosuccinate level from about 2% to about 22%, by weight, from about 3% to about 19%, by weight, 4% to about 17%, by weight, and/or from about 5% to about 15%, by weight. Suitable isethionate surfactants can include the reaction product of fatty acids esterified with isethionic acid and neutralized with sodium hydroxide. Suitable fatty acids for isethionate surfactants can be derived from coconut oil or palm kernel oil including amides of methyl tauride. Non-limiting examples of isethionates can be selected from the group consisting of sodium lauroyl methyl isethionate, sodium cocoyl isethionate, ammonium cocoyl isethionate, sodium hydrogenated cocoyl methyl isethionate, sodium lauroyl isethionate, sodium cocoyl methyl isethionate, sodium myristoyl isethionate, sodium oleoyl isethionate, sodium oleyl methyl isethionate, sodium palm kerneloyl isethionate, sodium stearoyl methyl isethionate, and mixtures thereof.

Non-limiting examples of sulfonates can include alpha olefin sulfonates, linear alkylbenzene sulfonates, sodium laurylglucosides hydroxypropylsulfonate and combination thereof.

Non-limiting examples of sulfoacetates can include sodium lauryl sulfoacetate, ammonium lauryl sulfoacetate and combination thereof.

Non-limiting example of glucose carboxylates can include sodium lauryl glucoside carboxylate, sodium cocoyl glucoside carboxylate and combinations thereof.

Non-limiting example of alkyl ether carboxylate can include sodium laureth-4 carboxylate, laureth-5 carboxylate, laureth-13 carboxylate, sodium C12-13 pareth-8 carboxylate, sodium C12-15 pareth-8 carboxylate and combination thereof.

Non-limiting example of acyl taurates can include sodium methyl cocoyl taurate, sodium methyl lauroyl taurate, sodium methyl oleoyl taurate and combination thereof.

The surfactant system may further comprise one or more amphoteric surfactants and the amphoteric surfactant can be selected from the group consisting of betaines, sultaines, hydroxysultanes, amphohydroxypropyl sulfonates, alkyl amphoactates, alkyl amphodiacetates and combination thereof.

Examples of betaine amphoteric surfactants can include coco dimethyl carboxymethyl betaine, cocoamidopropyl betaine (CAPB), cocobetaine, lauryl amidopropyl betaine (LAPB), oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, and mixtures thereof. Examples of sulfobetaines can include coco dimethyl sulfopropyl betaine, stearyl dimethyl sulfopropyl betaine, lauryl dimethyl sulfoethyl betaine, lauryl bis-(2-hydroxyethyl) sulfopropyl betaine and mixtures thereof.

Non-limiting example of alkylamphoacetates can include sodium cocoyl amphoacetate, sodium lauroyl amphoacetate and combination thereof.

The amphoteric surfactant can comprise cocamidopropyl betaine (CAPB), lauramidopropyl betaine (LAPB), and combinations thereof.

The cleansing composition can comprise an amphoteric surfactant level from about 0.5 wt % to about 20 wt %, from about 1 wt % to about 15 wt %, from about 2 wt % to about 13 wt %, from about 3 wt % to about 15 wt %, and/or from about 5 wt % to about 10 wt %.

The surfactant system can have a weight ratio of anionic surfactant to amphoteric surfactant from about 1:5 to about 10:1, from about 1:2 to about 7:1, from 1:1 to about 5:1, and/or from about 2:1 to about 4:1. The surfactant system can have a weight ratio of anionic surfactant to amphoteric surfactant greater than 1:1, greater than 3:2, greater than 9:5, and/or greater than 2:1. The surfactant system may further comprise one or more non-ionic surfactants and the non-ionic surfactant can be selected from the group consisting alkyl polyglucoside, alkyl glycoside, acyl glucamide and mixture thereof. Non-limiting examples of alkyl glucosides can include decyl glucoside, cocoyl glucoside, lauroyl glucoside and combination thereof.

Non-limiting examples of acyl glucamide can include lauroyl/myristoyl methyl glucamide, capryloyl/caproyl methyl glucamide, lauroyl/myristoyl methyl glucamide, The present invention may have from about 0.25% to about 15% of one or more amphoteric, nonionic or zwitterionic co-surfactants.

The present invention may have a pH of from about 5 to about 7; from about 5.5 to about 6.5; or from about 5.8 to about 6.

B. Cationic Polymers

The personal care composition also comprises a cationic polymer. These cationic polymers can include at least one of (a) a cationic guar polymer, (b) a cationic non-guar galactomannan polymer, (c) a cationic tapioca polymer, (d) a cationic copolymer of acrylamide monomers and cationic monomers, and/or (e) a synthetic, non-crosslinked, cationic polymer, which may or may not form lyotropic liquid crystals upon combination with the detersive surfactant (f) a cationic cellulose polymer. Additionally, the cationic polymer can be a mixture of cationic polymers.

The personal care composition may comprise a cationic guar polymer, which is a cationically substituted galactomannan (guar) gum derivatives. Guar gum for use in preparing these guar gum derivatives is typically obtained as a naturally occurring material from the seeds of the guar plant. The guar molecule itself is a straight chain mannan, which is branched at regular intervals with single membered galactose units on alternative mannose units. The mannose units are linked to each other by means of β(1-4) glycosidic linkages. The galactose branching arises by way of an α(1-6) linkage. Cationic derivatives of the guar gums are obtained by reaction between the hydroxyl groups of the polygalactomannan and reactive quaternary ammonium compounds. The degree of substitution of the cationic groups onto the guar structure should be sufficient to provide the requisite cationic charge density described above.

The cationic polymer may be, including but not limited to a cationic guar polymer, has a weight average Molecular weight of less than 2.2 million g/mol, or from about 150 thousand to about 2.2 million g/mol, or from about 200 thousand to about 2.2 million g/mol, or from about 300 thousand to about 1.2 million g/mol, or from about 750,000 thousand to about 1 million g/mol. The cationic guar polymer may have a charge density of from about 0.2 to about 2.2 meq/g, or from about 0.3 to about 2.0 meq/g, or from about 0.4 to about 1.8 meq/g; or from about 0.5 meq/g to about 1.8 meq/g.

The cationic polymers may have a molecular weight in the range of about 50,000 to less than or equal to 1.8 million and a charge density of about 0.5 to about 1.7 meq/g. The cationic polymer may be in the range of about 100,000 to about 1 million, in the range of about 500,000 to about 1.2 million. The cationic polymer may have a charge density of about 0.6 to about 1.2 meq/g; from about 0.8 to about 1.0 meq/g.

The cationic guar polymer may have a weight average Molecular weight of less than about 1.5 million g/mol, and has a charge density of from about 0.1 meq/g to about 2.5 meq/g. The cationic guar polymer may have a weight average molecular weight of less than 900 thousand g/mol, or from about 150 thousand to about 800 thousand g/mol, or from about 200 thousand to about 700 thousand g/mol, or from about 300 thousand to about 700 thousand g/mol, or from about 400 thousand to about 600 g/mol or from about 150 thousand to about 800 thousand g/mol, or from about 200 thousand to about 700 thousand g/mol, or from about 300 thousand to about 700 thousand g/mol, or from about 400 thousand to about 600 thousand g/mol. The cationic guar polymer may have a charge density of from about 0.2 to about 2.2 meq/g, or from about 0.3 to about 2.0 meq/g, or from about 0.4 to about 1.8 meq/g; or from about 0.5 meq/g to about 1.5 meq/g.

The cationic guar polymer may be formed from quaternary ammonium compounds. The quaternary ammonium compounds for forming the cationic guar polymer may conform to the general formula 1:

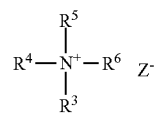

wherein where $R^3$, $R^4$ and $R^5$ are methyl or ethyl groups; $R^6$ is either an epoxyalkyl group of the general formula 2:

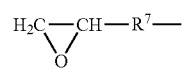

or $R^6$ is a halohydrin group of the general formula 3:

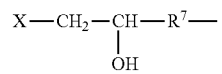

wherein $R^7$ is a $C_1$ to $C_3$ alkylene; X is chlorine or bromine, and Z is an anion such as Cl—, Br—, I— or $HSO_4$—.

The cationic guar polymer may conform to the general formula 4:

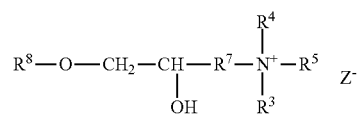

wherein $R^8$ is guar gum; and wherein $R^4$, $R^5$, $R^6$ and $R^7$ are as defined above; and wherein Z is a halogen. The cationic guar polymer may conform to Formula 5:

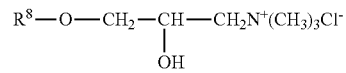

Suitable cationic guar polymers include cationic guar gum derivatives, such as guar hydroxypropyltrimonium chloride. The cationic guar polymer may be a guar hydroxypropyltrimonium chloride. Specific examples of guar hydroxypropyltrimonium chlorides include the Jaguar® series commercially available from Solvay, for example Jaguar® C-500, commercially available from Solvay. Jaguar® C-500 has a charge density of 0.8 meq/g and a molecular weight of 500,000 g/mol. Other suitable guar hydroxypropyltrimonium chloride are: guar hydroxypropyltrimonium chloride which has a charge density of about 1.3 meq/g and a molecular weight of about 500,000 g/mol and is available from Solvay as Jaguar® Optima. Other suitable guar hydroxypropyltrimonium chloride are: guar hydroxypropyltrimonium chloride which has a charge density of about 0.7 meq/g and a molecular weight of about 1,500,000 g/mol and is available from Solvay as Jaguar® Excel. Other suitable guar hydroxypropyltrimonium chloride are: guar hydroxypropyltrimonium chloride which has a charge density of about 1.1 meq/g and a molecular weight of about 500,000 g/mol and is available from ASI, a charge density of about 1.5 meq/g and a molecular weight of about 500,000 g/mole is available from ASI. Other suitable guar hydroxypropyltrimonium chloride are: Hi-Care 1000, which has a charge density of about 0.7 meq/g and a Molecular weight of about 600,000 g/mole and is available from Solvay; N-Hance 3269 and N-Hance 3270, which have a charge density of about 0.7 meq/g and a molecular weight of about 425,000 g/mol and are available from ASI; N-Hance 3196, which has a charge density of about 0.8 meq/g and a molecular weight of about 1,100,000 g/mol and is available from ASI. AquaCat CG518 has a charge density of about 0.9 meq/g and a Molecular weight of about 50,000 g/mol and is available from ASI. BF-13, which is a borate (boron) free guar of charge density of about 1 meq/g and molecular weight of about 800,000 and BF-17, which is a borate (boron) free guar of charge density of about 1.5 meq/g and molecular weight of about 800,000, and both are available from ASI.

The personal care compositions of the present invention may comprise a galactomannan polymer derivative having a mannose to galactose ratio of greater than 2:1 on a monomer to monomer basis, the galactomannan polymer derivative selected from the group consisting of a cationic galactomannan polymer derivative and an amphoteric galactomannan polymer derivative having a net positive charge. As used herein, the term "cationic galactomannan" refers to a galactomannan polymer to which a cationic group is added. The term "amphoteric galactomannan" refers to a galactomannan polymer to which a cationic group and an anionic group are added such that the polymer has a net positive charge.

Galactomannan polymers are present in the endosperm of seeds of the Leguminosae family Galactomannan polymers are made up of a combination of mannose monomers and galactose monomers. The galactomannan molecule is a straight chain mannan branched at regular intervals with single membered galactose units on specific mannose units. The mannose units are linked to each other by means of β (1-4) glycosidic linkages. The galactose branching arises by way of an α (1-6) linkage. The ratio of mannose monomers to galactose monomers varies according to the species of the plant and also is affected by climate. Non Guar Galactomannan polymer derivatives of the present invention have a ratio of mannose to galactose of greater than 2:1 on a monomer to monomer basis. Suitable ratios of mannose to galactose can be greater than about 3:1, and the ratio of mannose to galactose can be greater than about 4:1. Analysis of mannose to galactose ratios is well known in the art and is typically based on the measurement of the galactose content.

The gum for use in preparing the non-guar galactomannan polymer derivatives is typically obtained as naturally occurring material such as seeds or beans from plants. Examples of various non-guar galactomannan polymers include but are not limited to Tara gum (3 parts mannose/1 part galactose), Locust bean or Carob (4 parts mannose/1 part galactose), and *Cassia* gum (5 parts mannose/1 part galactose).

The non-guar galactomannan polymer derivatives may have a M. Wt. from about 1,000 to about 10,000,000, and/or from about 5,000 to about 3,000,000.

The personal care compositions of the invention can also include galactomannan polymer derivatives which have a cationic charge density from about 0.5 meq/g to about 7 meq/g. The galactomannan polymer derivatives can have a cationic charge density from about 1 meq/g to about 5 meq/g. The degree of substitution of the cationic groups onto the galactomannan structure should be sufficient to provide the requisite cationic charge density.

The galactomannan polymer derivative can be a cationic derivative of the non-guar galactomannan polymer, which is obtained by reaction between the hydroxyl groups of the polygalactomannan polymer and reactive quaternary ammonium compounds. Suitable quaternary ammonium compounds for use in forming the cationic galactomannan polymer derivatives include those conforming to the general formulas 1-5, as defined above.

Cationic non-guar galactomannan polymer derivatives formed from the reagents described above are represented by the general formula 6:

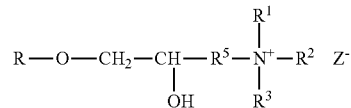

wherein R is the gum. The cationic galactomannan derivative can be a gum hydroxypropyltrimethylammonium chloride, which can be more specifically represented by the general formula 7:

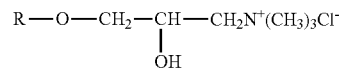

Alternatively the galactomannan polymer derivative can be an amphoteric galactomannan polymer derivative having a net positive charge, obtained when the cationic galactomannan polymer derivative further comprises an anionic group.

The cationic non-guar galactomannan can have a ratio of mannose to galactose is greater than about 4:1, a molecular weight of about 1,000 g/mol to about 10,000,000 g/mol, and/or from about 50,000 g/mol to about 1,000,000 g/mol, and/or from about 100,000 g/mol to about 900,000 g/mol, and/or from about 150,000 g/mol to about 400,000 g/mol and a cationic charge density from about 1 meq/g to about 5 meq/g, and/or from 2 meq/g to about 4 meq/g and can be derived from a *cassia* plant.

The personal care compositions can comprise water-soluble cationically modified starch polymers. As used herein, the term "cationically modified starch" refers to a starch to which a cationic group is added prior to degradation of the starch to a smaller molecular weight, or wherein a cationic group is added after modification of the starch to achieve a desired molecular weight. The definition of the term "cationically modified starch" also includes amphoterically modified starch. The term "amphoterically modified starch" refers to a starch hydrolysate to which a cationic group and an anionic group are added.

The cationically modified starch polymers disclosed herein have a percent of bound nitrogen of from about 0.5% to about 4%.

The cationically modified starch polymers for use in the personal care compositions can have a molecular weight about 850,000 g/mol to about 1,500,000 g/mol and/or from about 900,000 g/mol to about 1,500,000 g/mol.

The personal care compositions can include cationically modified starch polymers which have a charge density of from about 0.2 meq/g to about 5 meq/g, and/or from about 0.2 meq/g to about 2 meq/g. The chemical modification to obtain such a charge density includes, but is not limited to, the addition of amino and/or ammonium groups into the starch molecules. Non-limiting examples of these ammonium groups may include substituents such as hydroxypropyl trimmonium chloride, trimethylhydroxypropyl ammonium chloride, dimethylstearylhydroxypropyl ammonium chloride, and dimethyldodecylhydroxypropyl ammonium chloride. See Solarek, D. B., Cationic Starches in Modified Starches: Properties and Uses, Wurzburg, 0. B., Ed., CRC Press, Inc., Boca Raton, Fla. 1986, pp 113-125. The cationic groups may be added to the starch prior to degradation to a smaller molecular weight or the cationic groups may be added after such modification.

The cationically modified starch polymers generally have a degree of substitution of a cationic group from about 0.2 to about 2.5. As used herein, the "degree of substitution" of the cationically modified starch polymers is an average measure of the number of hydroxyl groups on each anhydroglucose unit which is derivatized by substituent groups. Since each anhydroglucose unit has three potential hydroxyl groups available for substitution, the maximum possible degree of substitution is 3. The degree of substitution is expressed as the number of moles of substituent groups per mole of anhydroglucose unit, on a molar average basis. The degree of substitution may be determined using proton nuclear magnetic resonance spectroscopy (".sup.1H NMR") methods well known in the art. Suitable .sup.1H NMR techniques include those described in "Observation on NMR Spectra of Starches in Dimethyl Sulfoxide, Iodine-Complexing, and Solvating in Water-Dimethyl Sulfoxide", Qin-Ji Peng and Arthur S. Perlin, Carbohydrate Research, 160 (1987), 57-72; and "An Approach to the Structural Analysis of Oligosaccharides by NMR Spectroscopy", J. Howard Bradbury and J. Grant Collins, Carbohydrate Research, 71, (1979), 15-25.

The source of starch before chemical modification can be chosen from a variety of sources such as tubers, legumes, cereal, and grains. Non-limiting examples of this source starch may include corn starch, wheat starch, rice starch, waxy corn starch, oat starch, cassava starch, waxy barley, waxy rice starch, glutenous rice starch, sweet rice starch, amioca, potato starch, tapioca starch, oat starch, sago starch, sweet rice, or mixtures thereof.

The cationically modified starch polymers can be selected from degraded cationic maize starch, cationic tapioca, cationic potato starch, and mixtures thereof. Alternatively, the cationically modified starch polymers are cationic corn starch and cationic tapioca.

The starch, prior to degradation or after modification to a smaller molecular weight, may comprise one or more additional modifications. For example, these modifications may include cross-linking, stabilization reactions, phosphorylations, and hydrolyzations. Stabilization reactions may include alkylation and esterification.

The cationically modified starch polymers may be incorporated into the composition in the form of hydrolyzed starch (e.g., acid, enzyme, or alkaline degradation), oxidized starch (e.g., peroxide, peracid, hypochlorite, alkaline, or any other oxidizing agent), physically/mechanically degraded starch (e.g., via the thermo-mechanical energy input of the processing equipment), or combinations thereof.

An optimal form of the starch is one which is readily soluble in water and forms a substantially clear (% Transmittance of about 80 at 600 nm) solution in water. The transparency of the composition is measured by Ultra-Violet/Visible (UV/VIS) spectrophotometry, which determines the absorption or transmission of UV/VIS light by a sample, using a Gretag Macbeth Colorimeter Color i 5 according to the related instructions. A light wavelength of 600 nm has been shown to be adequate for characterizing the degree of clarity of cosmetic compositions.

Suitable cationically modified starch for use in personal care compositions are available from known starch suppliers. Also suitable for use in personal care compositions are nonionic modified starch that can be further derivatized to a cationically modified starch as is known in the art. Other suitable modified starch starting materials may be quaternized, as is known in the art, to produce the cationically modified starch polymer suitable for use in personal care compositions.

Starch Degradation Procedure: a starch slurry can be prepared by mixing granular starch in water. The temperature is raised to about 35° C. An aqueous solution of potassium permanganate is then added at a concentration of about 50 ppm based on starch. The pH is raised to about 11.5 with sodium hydroxide and the slurry is stirred sufficiently to prevent settling of the starch. Then, about a 30% solution of hydrogen peroxide diluted in water is added to a level of about 1% of peroxide based on starch. The pH of about 11.5 is then restored by adding additional sodium hydroxide. The reaction is completed over about a 1 to about 20 hour period. The mixture is then neutralized with dilute hydrochloric acid. The degraded starch is recovered by filtration followed by washing and drying.

The personal care composition can comprise a cationic copolymer of an acrylamide monomer and a cationic monomer, wherein the copolymer has a charge density of from about 1.0 meq/g to about 3.0 meq/g. The cationic copolymer can be a synthetic cationic copolymer of acrylamide monomers and cationic monomers.

The cationic copolymer can comprise:

(i) an acrylamide monomer of the following Formula AM:

Formula AM

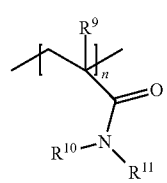

where $R^9$ is H or $C_{1-4}$ alkyl; and $R^{19}$ and $R^{11}$ are independently selected from the group consisting of H, $C_{1-4}$ alkyl, $CH_2OCH_3$, $CH_2OCH_2CH(CH_3)_2$, and phenyl, or together are $C_{3-6}$cycloalkyl; and
(ii) a cationic monomer conforming to Formula CM:

Formula CM

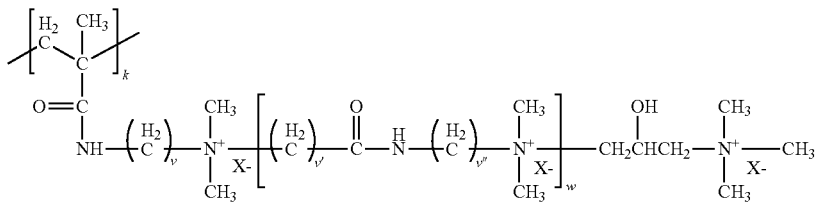

where k=1, each of v, v', and v" is independently an integer of from 1 to 6, w is zero or an integer of from 1 to 10, and $X^-$ is an anion.

The cationic monomer can conform to Formula CM and where k=1, v=3 and w=0, z=1 and $X^-$ is $Cl^-$ to form the following structure:

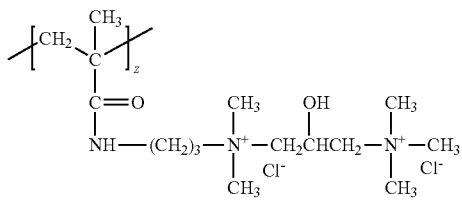

The above structure may be referred to as diquat. Alternatively, the cationic monomer can conform to Formula CM and wherein v and v" are each 3, v'=1, w=1, y=1 and $X^-$ is $Cl^-$, such as:

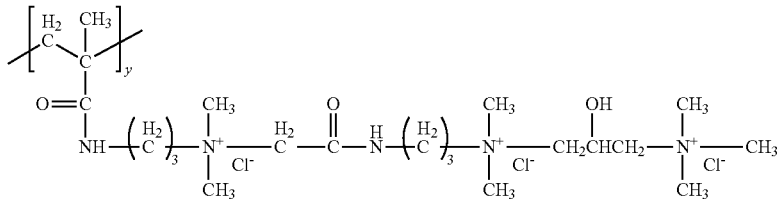

The above structure may be referred to as triquat.

Suitable acrylamide monomer include, but are not limited to, either acrylamide or methacrylamide.

The cationic copolymer (b) can be AM:TRIQUAT which is a copolymer of acrylamide and 1,3-Propanediaminium, N-[2-[[[dimethyl[3-[(2-methyl-1-oxo-2-propenyl)amino]propyl]ammonio]acetyl]amino]ethyl]2-hydroxy-N,N,N',N'-pentamethyl-, trichloride. AM:TRIQUAT is also known as polyquaternium-76 (PQ76). AM:TRIQUAT may have a charge density of 1.6 meq/g and a molecular weight of 1.1 million g/mol.

The cationic copolymer may be of an acrylamide monomer and a cationic monomer, wherein the cationic monomer is selected from the group consisting of: dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide; ethylenimine, vinylamine, 2-vinylpyridine, 4-vinylpyridine; trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride, and mixtures thereof.

The cationic copolymer can comprise a cationic monomer selected from the group consisting of: cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, and mixtures thereof.

The cationic copolymer can be water-soluble. The cationic copolymer is formed from (1) copolymers of (meth)acrylamide and cationic monomers based on (meth)acrylamide, and/or hydrolysis-stable cationic monomers, (2) terpolymers of (meth)acrylamide, monomers based on cationic (meth)acrylic acid esters, and monomers based on (meth)acrylamide, and/or hydrolysis-stable cationic monomers. Monomers based on cationic (meth)acrylic acid esters may be cationized esters of the (meth)acrylic acid containing a quaternized N atom. The cationized esters of the (meth)acrylic acid containing a quaternized N atom may be quaternized dialkylaminoalkyl (meth)acrylates with C1 to C3 in the alkyl and alkylene groups. Suitable cationized esters of the (meth)acrylic acid containing a quaternized N atom can be selected from the group consisting of: ammonium salts of dimethylaminomethyl (meth)acrylate, dimethylaminoethyl (meth)acrylate, dimethylaminopropyl (meth)acrylate, diethylaminomethyl (meth)acrylate, diethylaminoethyl (meth)acrylate; and diethylaminopropyl (meth)acrylate quaternized with methyl chloride. The cationized esters of the (meth)acrylic acid containing a quaternized N atom may be dimethylaminoethyl acrylate, which is quaternized with an alkyl halide, or with methyl chloride or benzyl chloride or dimethyl sulfate (ADAME-Quat). the cationic monomer when based on (meth)acrylamides can be quaternized dialkylaminoalkyl(meth)acrylamides with C1 to C3 in the alkyl and alkylene groups, or dimethylaminopropylacrylamide, which is quaternized with an alkyl halide, or methyl chloride or benzyl chloride or dimethyl sulfate.

Suitable cationic monomer based on a (meth)acrylamide include quaternized dialkylaminoalkyl(meth)acrylamide with C1 to C3 in the alkyl and alkylene groups. The cationic monomer based on a (meth)acrylamide can be dimethylaminopropylacrylamide, which is quaternized with an alkyl halide, especially methyl chloride or benzyl chloride or dimethyl sulfate.

The cationic monomer can be a hydrolysis-stable cationic monomer. Hydrolysis-stable cationic monomers can be, in addition to a dialkylaminoalkyl(meth)acrylamide, all monomers that can be regarded as stable to the OECD hydrolysis test. The cationic monomer can be hydrolysis-stable and the hydrolysis-stable cationic monomer can be selected from the group consisting of: diallyldimethylammonium chloride and water-soluble, cationic styrene derivatives.

The cationic copolymer can be a terpolymer of acrylamide, 2-dimethylammoniumethyl (meth)acrylate quaternized with methyl chloride (ADAME-Q) and 3-dimethylammoniumpropyl(meth)acrylamide quaternized with methyl chloride (DIMAPA-Q). The cationic copolymer can be formed from acrylamide and acrylamidopropyltrimethylammonium chloride, wherein the acrylamidopropyltrimethylammonium chloride has a charge density of from about 1.0 meq/g to about 3.0 meq/g.

The cationic copolymer can have a charge density of from about 1.1 meq/g to about 2.5 meq/g, or from about 1.1 meq/g to about 2.3 meq/g, or from about 1.2 meq/g to about 2.2 meq/g, or from about 1.2 meq/g to about 2.1 meq/g, or from about 1.3 meq/g to about 2.0 meq/g, or from about 1.3 meq/g to about 1.9 meq/g.

The cationic copolymer can have a molecular weight from about 100 thousand g/mol to about 1.5 million g/mol, or from about 300 thousand g/mol to about 1.5 million g/mol, or from about 500 thousand g/mol to about 1.5 million g/mol, or from about 700 thousand g/mol to about 1.0 million g/mol, or from about 900 thousand g/mol to about 1.2 million g/mol.

The cationic copolymer can be a trimethylammoniopropylmethacrylamide chloride-N-Acrylamide copolymer, which is also known as AM:MAPTAC. AM:MAPTAC may have a charge density of about 1.3 meq/g and a molecular weight of about 1.1 million g/mol. The cationic copolymer can be AM:ATPAC. AM:ATPAC can have a charge density of about 1.8 meq/g and a molecular weight of about 1.1 million g/mol.

(a) Cationic Synthetic Polymers

The personal care composition can comprise a cationic synthetic polymer that may be formed from
  i) one or more cationic monomer units, and optionally
  ii) one or more monomer units bearing a negative charge, and/or
  iii) a nonionic monomer,
wherein the subsequent charge of the copolymer is positive. The ratio of the three types of monomers is given by "m", "p" and "q" where "m" is the number of cationic monomers, "p" is the number of monomers bearing a negative charge and "q" is the number of nonionic monomers The cationic polymers can be water soluble or dispersible, non-crosslinked, and synthetic cationic polymers having the following structure:

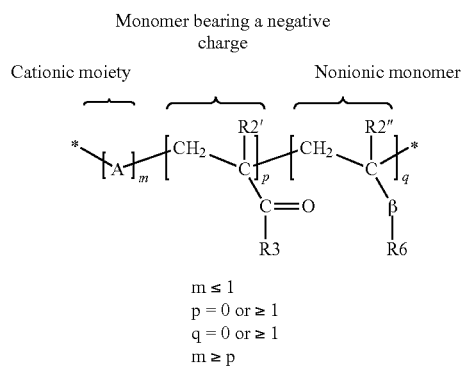

where A, may be one or more of the following cationic moieties:

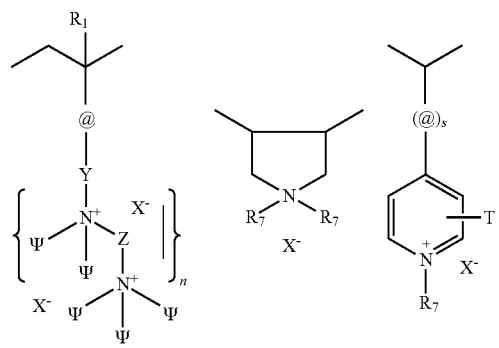

where @=amido, alkylamido, ester, ether, alkyl or alkylaryl;
where Y=C1-C22 alkyl, alkoxy, alkylidene, alkyl or aryloxy;
where ψ=C1-C22 alkyl, alkyloxy, alkyl aryl or alkyl arylox;
where Z=C1-C22 alkyl, alkyloxy, aryl or aryloxy;
where R1=H, C1-C4 linear or branched alkyl;
where s=0 or 1, n=0 or ≥1;
where T and R7=C1-C22 alkyl; and
where X—=halogen, hydroxide, alkoxide, sulfate or alkylsulfate.

Where the monomer bearing a negative charge is defined by R2'=H, C1-C4 linear or branched alkyl and R3 as:

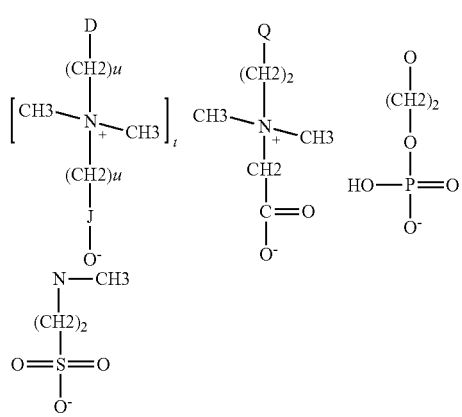

where D=O, N, or S;
where Q=NH$_2$ or O;

where u=1-6;
where t=0-1; and
where J=oxygenated functional group containing the following elements P, S, C.

Where the nonionic monomer is defined by R2"=H, C1-C4 linear or branched alkyl, R6=linear or branched alkyl, alkyl aryl, aryl oxy, alkyloxy, alkylaryl oxy and β is defined as

and
where G' and G" are, independently of one another, O, S or N—H and L=0 or 1.

Examples of cationic monomers include aminoalkyl (meth)acrylates, (meth)aminoalkyl (meth)acrylamides; monomers comprising at least one secondary, tertiary or quaternary amine function, or a heterocyclic group containing a nitrogen atom, vinylamine or ethylenimine; diallyldialkyl ammonium salts; their mixtures, their salts, and macromonomers deriving from therefrom.

Further examples of cationic monomers include dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide, ethylenimine, vinylamine, 2-vinylpyridine, 4-vinylpyridine, trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride.

Suitable cationic monomers include those which comprise a quaternary ammonium group of formula —NR$_3^+$, wherein R, which is identical or different, represents a hydrogen atom, an alkyl group comprising 1 to 10 carbon atoms, or a benzyl group, optionally carrying a hydroxyl group, and comprise an anion (counter-ion). Examples of anions are halides such as chlorides, bromides, sulphates, hydrosulphates, alkylsulphates (for example comprising 1 to 6 carbon atoms), phosphates, citrates, formates, and acetates.

Suitable cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride.

Additional suitable cationic monomers include trimethyl ammonium propyl (meth)acrylamido chloride.

Examples of monomers bearing a negative charge include alpha ethylenically unsaturated monomers comprising a phosphate or phosphonate group, alpha ethylenically unsaturated monocarboxylic acids, monoalkylesters of alpha ethylenically unsaturated dicarboxylic acids, monoalkylamides of alpha ethylenically unsaturated dicarboxylic acids, alpha ethylenically unsaturated compounds comprising a sulphonic acid group, and salts of alpha ethylenically unsaturated compounds comprising a sulphonic acid group.

Suitable monomers with a negative charge include acrylic acid, methacrylic acid, vinyl sulphonic acid, salts of vinyl sulfonic acid, vinylbenzene sulphonic acid, salts of vinylbenzene sulphonic acid, alpha-acrylamidomethylpropanesulphonic acid, salts of alpha-acrylamidomethylpropanesulphonic acid, 2-sulphoethyl methacrylate, salts of 2-sulphoethyl methacrylate, acrylamido-2-methylpropanesulphonic acid (AMPS), salts of acrylamido-2-methylpropanesulphonic acid, and styrenesulphonate (SS).

Examples of nonionic monomers include vinyl acetate, amides of alpha ethylenically unsaturated carboxylic acids, esters of an alpha ethylenically unsaturated monocarboxylic acids with an hydrogenated or fluorinated alcohol, polyethylene oxide (meth)acrylate (i.e. polyethoxylated (meth)acrylic acid), monoalkylesters of alpha ethylenically unsaturated dicarboxylic acids, monoalkylamides of alpha ethylenically unsaturated dicarboxylic acids, vinyl nitriles, vinylamine amides, vinyl alcohol, vinyl pyrolidone, and vinyl aromatic compounds.

Suitable nonionic monomers include styrene, acrylamide, methacrylamide, acrylonitrile, methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, 2-ethyl-hexyl methacrylate, 2-hydroxyethylacrylate and 2-hydroxyethylmethacrylate.

The anionic counterion (X—) in association with the synthetic cationic polymers may be any known counterion so long as the polymers remain soluble or dispersible in water, in the personal care composition, or in a coacervate phase of the personal care composition, and so long as the counterions are physically and chemically compatible with the essential components of the personal care composition or do not otherwise unduly impair product performance, stability or aesthetics. Non limiting examples of such counterions include halides (e.g., chlorine, fluorine, bromine, iodine), sulfate and methylsulfate.

The cationic polymer described herein can aid in providing damaged hair, particularly chemically treated hair, with a surrogate hydrophobic F-layer. The microscopically thin F-layer provides natural weatherproofing, while helping to seal in moisture and prevent further damage. Chemical treatments damage the hair cuticle and strip away its protective F-layer. As the F-layer is stripped away, the hair becomes increasingly hydrophilic. It has been found that when lyotropic liquid crystals are applied to chemically treated hair, the hair becomes more hydrophobic and more virgin-like, in both look and feel. Without being limited to any theory, it is believed that the lyotropic liquid crystal complex creates a hydrophobic layer or film, which coats the hair fibers and protects the hair, much like the natural F-layer protects the hair. The hydrophobic layer returns the hair to a generally virgin-like, healthier state. Lyotropic liquid crystals are formed by combining the synthetic cationic polymers described herein with the aforementioned anionic detersive surfactant component of the personal care composition. The synthetic cationic polymer has a relatively high charge density. It should be noted that some synthetic polymers having a relatively high cationic charge density do not form lyotropic liquid crystals, primarily due to their abnormal linear charge densities. Such synthetic cationic polymers are described in WO 94/06403 to Reich et al. The synthetic polymers described herein can be formulated in a stable personal care composition that provides improved conditioning performance, with respect to damaged hair.

Cationic synthetic polymers that can form lyotropic liquid crystals have a cationic charge density of from about 2 meq/gm to about 7 meq/gm, and/or from about 3 meq/gm to about 7 meq/gm, and/or from about 4 meq/gm to about 7 meq/gm. The cationic charge density may be about 6.2 meq/gm. The polymers also have a M. Wt. of from about 1,000 to about 5,000,000, and/or from about 10,000 to about 1,500,000, and/or from about 100,000 to about 1,500,000.

In the invention cationic synthetic polymers that provide enhanced conditioning and deposition of benefit agents but do not necessarily form lyotropic liquid crystals may have a cationic charge density of from about 0.7 meq/gm to about 7 meq/gm, and/or from about 0.8 meq/gm to about 5 meq/gm, and/or from about 1.0 meq/gm to about 3 meq/gm. The polymers may also have a M. Wt. of from about 1,000 to about 1,500,000, from about 10,000 to about 1,500,000, and from about 100,000 to about 1,500,000.

Suitable cationic cellulose polymers are salts of hydroxyethyl cellulose reacted with trimethyl ammonium substituted epoxide, referred to in the industry (CTFA) as Polyquaternium-10 and available from Dow/Amerchol Corp. (Edison, N.J., USA) in their Polymer LR, JR, and KG series of polymers. Non-limiting examples include: JR-30M, KG-30M, JP, LR-400 and mixtures thereof. Other suitable types of cationic cellulose include the polymeric quaternary ammonium salts of hydroxyethyl cellulose reacted with lauryl dimethyl ammonium-substituted epoxide referred to in the industry (CTFA) as Polyquaternium-24. These materials are available from Dow/Amerchol Corp. under the tradename Polymer LM-200. Other suitable types of cationic cellulose include the polymeric quaternary ammonium salts of hydroxyethyl cellulose reacted with lauryl dimethyl ammonium-substituted epoxide and trimethyl ammonium substituted epoxide referred to in the industry (CTFA) as Polyquaternium-67. These materials are available from Dow/Amerchol Corp. under the tradename SoftCAT Polymer SL-5, SoftCAT Polymer SL-30, Polymer SL-60, Polymer SL-100, Polymer SK-L, Polymer SK-M, Polymer SK-MH, and Polymer SK-H.

The concentration of the cationic polymers ranges about 0.025% to about 5%, from about 0.1% to about 3%, from about 0.1% to about 1.2%, from about 0.2% to about 1%, from about 0.6% to about 0.9%, by weight of the personal care composition.

Rheology Polymer

The personal care composition can comprise a rheology polymer to increase the viscosity of the composition. Suitable rheology polymers can be used. The personal care composition can comprise from about 0.1% to about 1.2% of a rheology polymer, from about 0.4% to about 0.8% of a rheology polymer, and from about 0.5% to about 0.7% of a rheology polymer. The rheology polymer modifier may be a polyacrylate, polyacrylamide thickeners. The rheology polymer may be an anionic rheology polymer.

The personal care composition may comprise rheology polymers that are homopolymers based on acrylic acid, methacrylic acid or other related derivatives, non-limiting examples include polyacrylate, polymethacrylate, polyethylacrylate, and polyacrylamide.

The rheology polymers may be alkali swellable and hydrophobically-modified alkali swellable acrylic copolymers or methacrylate copolymers, non-limiting examples include acrylic acid/acrylonitrogens copolymer, acrylates/steareth-20 itaconate copolymer, acrylates/ceteth-20 itaconate copolymer, Acrylates/Aminoacrylates/C10-30 Alkyl PEG-20 Itaconate Copolymer, acrylates/aminoacrylates copolymer, acrylates/steareth-20 methacrylate copolymer, acrylates/beheneth-25 methacrylate copolymer, acrylates/steareth-20 methacrylate crosspolymer, acrylates/beheneth-25 methacrylate/HEMA crosspolymer, acrylates/vinyl neodecanoate crosspolymer, acrylates/vinyl isodecanoate crosspolymer, Acrylates/Palmeth-25 Acrylate Copolymer, Acrylic Acid/Acrylamidomethyl Propane Sulfonic Acid Copolymer, and acrylates/C10-C30 alkyl acrylate crosspolymer. The rheology polymer may be an anionic acrylic copolymer polymer considered an ASE polymer or Alkali Swellable emulsion polymer as defined by BASF the supplier.

The rheology polymers may be soluble crosslinked acrylic polymers, a non-limiting example includes carbomers.

The rheology polymers may be an associative polymeric thickeners, non-limiting examples include: hydrophobically modified, alkali swellable emulsions, non-limiting examples include hydrophobically modified polypolyacrylates; hydrophobically modified polyacrylic acids, and hydrophobically modified polyacrylamides; hydrophobically modified polyethers wherein these materials may have a hydrophobe that can be selected from cetyl, stearyl, oleayl, and combinations thereof.

The rheology polymers may be used in combination with polyvinylpyrrolidone, crosslinked polyvinylpyrrolidone and derivatives. The rheology polymers may be combined with polyvinylalcohol and derivatives. The rheology polymers may be combined with polyethyleneimine and derivatives.

The rheology polymers may be combined with alginic acid based materials, non-limiting examples include sodium alginate, and alginic acid propylene glycol esters.

The rheology polymers may be used in combination with polyurethane polymers, non-limiting examples include: hydrophobically modified alkoxylated urethane polymers, non-limiting examples include PEG-150/decyl alcohol/SMDI copolymer, PEG-150/stearyl alcohol/SMDI copolymer, polyurethane-39.

The rheology polymers may be combined with an associative polymeric thickeners, or an associative thickening polymer non-limiting examples include: hydrophobically modified cellulose derivatives; and a hydrophilic portion of repeating ethylene oxide groups with repeat units from 10-300, from 30-200, and from 40-150. Non-limiting examples of this class include PEG-120-methylglucose dioleate, PEG-(40 or 60) sorbitan tetraoleate, PEG-150 pentaerythrityl tetrastearate, PEG-55 propylene glycol oleate, PEG-150 distearate.

The rheology polymers may be combined with cellulose and derivatives, non-limiting examples include microcrystalline cellulose, carboxymethylcelluloses, hydroxyethylcellulose, hydroxypropylcellulose, hydroxypropyl methylcellulose, methylcellulose, ethyl cellulose; nitro cellulose; cellulose sulfate; cellulose powder; hydrophobically modified celluloses.

The rheology polymers may be combined with a guar and guar derivatives, non-limiting examples include hydroxypropyl guar, and hydroxypropyl guar hydroxypropyl trimonium chloride.

The rheology polymers may be combined with polyethylene oxide; polypropylene oxide; and POE-PPO copolymers.

The rheology polymers may be combined with polyalkylene glycols characterized by the general formula:

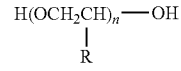

wherein R is hydrogen, methyl, or mixtures thereof, preferably hydrogen, and n is an integer having an average from 2,000-180,000, or from 7,000-90,000, or from 7,000-45,000. Non-limiting examples of this class include PEG-7M, PEG-14M, PEG-23M, PEG-25M, PEG-45M, PEG-90M, or PEG-100M.

The rheology polymers may be combined with silicas, non-limiting examples include fumed silica, precipitated silica, and silicone-surface treated silica.

The rheology polymers may be combined with water-swellable clays, non-limiting examples include laponite, bentolite, montmorilonite, smectite, and hectonite.

The rheology polymers may be combined with gums, non-limiting examples include xanthan gum, guar gum, hydroxypropyl guar gum, Arabia gum, tragacanth, galactan, carob gum, karaya gum, and locust bean gum.

The rheology polymers may be combined with, dibenzylidene sorbitol, karaggenan, pectin, agar, quince seed (*Cydonia oblonga* Mill), starch (from rice, corn, potato, wheat, etc), starch-derivatives (e.g. carboxymethyl starch, methylhydroxypropyl starch), algae extracts, dextran, succinoglucan, and pulleran, Non-limiting examples of rheology polymers include acrylamide/ammonium acrylate copolymer (and) polyisobutene (and) polysorbate 20; acrylamide/sodium acryloyldimethyl taurate copolymer/isohexadecane/polysorbate 80, ammonium acryloyldimethyltaurate/VP copolymer, Sodium Acrylate/Sodium Acryloyldimethyl Taurate Copolymer, acrylates copolymer, Acrylates Crosspolymer-4, Acrylates Crosspolymer-3, acrylates/beheneth-25 methacrylate copolymer, acrylates/C10-C30 alkyl acrylate crosspolymer, acrylates/steareth-20 itaconate copolymer, ammonium polyacrylate/Isohexadecane/PEG-40 castor oil; carbomer, sodium carbomer, cross-linked polyvinylpyrrolidone (PVP), polyacrylamide/C13-14 isoparaffin/laureth-7, polyacrylate 13/polyisobutene/polysorbate 20, polyacrylate crosspolymer-6, polyamide-3, polyquaternium-37 (and) hydrogenated polydecene (and) trideceth-6, Acrylamide/Sodium Acryloyldimethyltaurate/Acrylic Acid Copolymer, sodium acrylate/acryloyldimethyltaurate/dimethylacrylamide, crosspolymer (and) isohexadecane (and) polysorbate 60, sodium polyacrylate. Exemplary commercially-available rheology polymers include ACULYN™ 28, ACULYN™ 88, ACULYN™ 33, ACULYN™ 22, ACULYN™ Excel, Carbopol® Aqua SF-1, Carbopol® ETD 2020, Carbopol® Ultrez 20, Carbopol® Ultrez 21, Carbopol® Ultrez 10, Carbopol® Ultrez 30, Carbopol® 1342, Carbopol® Aqua SF-2 Polymer, Sepigel™ 305, Simulgel™ 600, Sepimax Zen, Carbopol® SMART 1000, Rheocare® TTA, Rheomer® SC-Plus, STRUCTURE® PLUS, Aristoflex® AVC, Stabylen 30, and combinations thereof.

1. Water Miscible Solvents

The carrier of the personal care composition may include water and water solutions of lower alkyl alcohols, polyhydric alcohols, ketones having from 3 to 4 carbons atoms, C1-C6 esters of C1-C6 alcohols, sulfoxides, amides, carbonate esters, ethoxylated and proposylated C1-C10 alcohols, lactones, pyrollidones, and mixtures thereof. Non-limited lower alkyl alcohol examples are monohydric alcohols having 1 to 6 carbons, such as ethanol and isopropanol. Non-limiting examples of polyhydric alcohols useful herein include propylene glycol, dipropylene glycol, butylenes glycol, hexylene glycol, glycerin, propane diol and mixtures thereof.

In present invention, the personal care composition may comprise a hydrotrope/viscosity modifier which is an alkali metal or ammonium salt of a lower alkyl benzene sulphonate such as sodium xylene sulphonate, sodium cumene sulphonate or sodium toluene sulphonate.

In the present invention, the personal care composition may comprise silicone/PEG-8 silicone/PEG-9 silicone/PEG-n silicone/silicone ether (n could be another integer), non-limiting examples include PEGS-dimethicone A208) MW 855, PEG 8 Dimethicone D208 MW 2706.

C. Scalp Health Agents

In the present invention, one or more scalp health agent may be added to provide scalp benefits in addition to the anti-fungal/anti-dandruff efficacy provided by the surfactant soluble anti-dandruff agents. This group of materials is varied and provides a wide range of benefits including moisturization, barrier improvement, anti-fungal, anti-microbial and anti-oxidant, anti-itch, and sensates, and additional anti-dandruff agents. Such scalp health agents include but are not limited to: vitamin E and F, salicylic acid, niacinamide, caffeine, panthenol, zinc oxide, zinc carbonate, basic zinc carbonate, glycols, glycolic acid, PCA, PEGs, erythritol, glycerin, triclosan, lactates, hyaluronates, allantoin and other ureas, betaines, sorbitol, glutamates, xylitols, menthol, menthyl lactate, iso cyclomone, benzyl alcohol, a compound comprising the following structure:

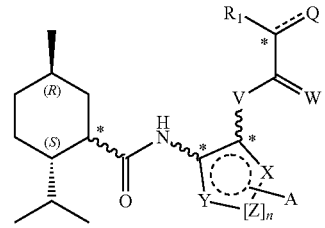

$R_1$ is selected from H, alkyl, amino alkyl, alkoxy;
$Q=H_2$, O, $-OR_1$, $-N(R_1)_2$, $-OPO(OR_1)_x$, $-PO(OR_1)_x$, $-P(OR_1)_x$ where x=1-2;
$V=NR_1$, O, $-OPO(OR_1)_x$, $-PO(OR_1)_x$, $-P(OR_1)_x$ where x=1-2;
$W=H_2$, O;
X, Y=independently selected from H, aryl, naphthyl for n=0;
X, Y=aliphatic $CH_2$ or aromatic CH for n≥1 and Z is selected from aliphatic $CH_2$, aromatic CH, or heteroatom;
A=lower alkoxy, lower alkylthio, aryl, substituted aryl or fused aryl; and stereochemistry is variable at the positions marked*.

and natural extracts/oils including peppermint, spearmint, argan, jojoba and aloe.

D. Optional Ingredients

In the present invention, the personal care composition may further comprise one or more optional ingredients, including benefit agents. Suitable benefit agents include, but are not limited to conditioning agents, cationic polymers, silicone emulsions, anti-dandruff agents, gel networks, chelating agents, and natural oils such as sun flower oil or castor oil. Additional suitable optional ingredients include but are not limited to perfumes, perfume microcapsules, colorants, particles, anti-microbials, foam busters, anti-static agents, rheology modifiers and thickeners, suspension materials and structurants, pH adjusting agents and buffers, preservatives, pearlescent agents, solvents, diluents, anti-oxidants, vitamins and combinations thereof. In the present invention, a perfume may be present from about 0.5% to about 7%.

Such optional ingredients should be physically and chemically compatible with the components of the composition, and should not otherwise unduly impair product stability, aesthetics, or performance. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of non-limiting materials that can be added to the composition herein.

1. Conditioning Agents

The conditioning agent of the personal care compositions can be a silicone conditioning agent. The silicone conditioning agent may comprise volatile silicone, non-volatile silicone, or combinations thereof. The concentration of the silicone conditioning agent typically ranges from about 0.01% to about 10%, by weight of the composition, from about 0.1% to about 8%, from about 0.1% to about 5%, and/or from about 0.2% to about 3%. Non-limiting examples of suitable silicone conditioning agents, and optional suspending agents for the silicone, are described in U.S. Reissue Pat. No. 34,584, U.S. Pat. Nos. 5,104,646, and 5,106,609, which descriptions are incorporated herein by reference.

The silicone conditioning agents for use in the compositions of the present invention can have a viscosity, as measured at 25° C., from about 20 to about 2,000,000 centistokes ("csk"), from about 1,000 to about 1,800,000 csk, from about 10,000 to about 1,500,000 csk, and/or from about 20,000 to about 1,500,000 csk.

The dispersed silicone conditioning agent particles typically have a volume average particle diameter ranging from about 0.01 micrometer to about 60 micrometer. For small particle application to hair, the volume average particle diameters typically range from about 0.01 micrometer to about 4 micrometer, from about 0.01 micrometer to about 2 micrometer, from about 0.01 micrometer to about 0.5 micrometer.

Additional material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989), incorporated herein by reference.

Silicone emulsions suitable for use in the present invention may include, but are not limited to, emulsions of insoluble polysiloxanes prepared in accordance with the descriptions provided in U.S. Pat. No. 6,316,541 or 4,476,282 or U.S. Patent Application Publication No. 2007/0276087. Accordingly, suitable insoluble polysiloxanes include polysiloxanes such as alpha, omega hydroxy-terminated polysiloxanes or alpha, omega alkoxy-terminated polysiloxanes having an internal phase viscosity from about 5 csk to about 500,000 csk. For example, the insoluble polysiloxane may have an internal phase viscosity less 400,000 csk, preferably less than 200,000 csk, more preferably from about 10,000 csk to about 180,000 csk. The insoluble polysiloxane can have an average particle size within the range from about 10 nm to about 10 micron. The average particle size may be within the range from about 15 nm to about 5 micron, from about 20 nm to about 1 micron, or from about 25 nm to about 500 nm.

The average molecular weight of the insoluble polysiloxane, the internal phase viscosity of the insoluble polysiloxane, the viscosity of the silicone emulsion, and the size of the particle comprising the insoluble polysiloxane are determined by methods commonly used by those skilled in the art, such as the methods disclosed in Smith, A. L. *The Analytical Chemistry of Silicones*, John Wiley & Sons, Inc.: New York, 1991. For example, the viscosity of the silicone emulsion can be measured at 30° C. with a Brookfield viscometer with spindle 6 at 2.5 rpm. The silicone emulsion may further include an additional emulsifier together with the anionic surfactant, Other classes of silicones suitable for use in compositions of the present invention include but are not limited to: i) silicone fluids, including but not limited to, silicone oils, which are flowable materials having viscosity less than about 1,000,000 csk as measured at 25° C.; ii) aminosilicones, which contain at least one primary, secondary or tertiary amine; iii) cationic silicones, which contain at least one quaternary ammonium functional group; iv) silicone gums; which include materials having viscosity greater or equal to 1,000,000 csk as measured at 25° C.; v) silicone resins, which include highly cross-linked polymeric siloxane systems; vi) high refractive index silicones, having refractive index of at least 1.46, and vii) mixtures thereof.

The conditioning agent of the personal care compositions of the present invention may also comprise at least one organic conditioning material such as oil or wax, either alone or in combination with other conditioning agents, such as the silicones described above. The organic material can be non-polymeric, oligomeric or polymeric. It may be in the form of oil or wax and may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-200, PEG-400, PEG-600, PEG-1000, PEG-2M, PEG-7M, PEG-14M, PEG-45M and mixtures thereof.

Gel Network

In the present invention, a gel network may be present. The gel network component of the present invention comprises at least one fatty amphiphile. As used herein, "fatty amphiphile" refers to a compound having a hydrophobic tail group as defined as an alkyl, alkenyl (containing up to 3 double bonds), alkyl aromatic, or branched alkyl group of $C_{12}$-$C_{70}$ length and a hydrophilic head group which does not make the compound water soluble, wherein the compound also has a net neutral charge at the pH of the shampoo composition.

The shampoo compositions of the present invention comprise fatty amphiphile as part of the pre-formed dispersed gel network phase in an amount from about 0.05% to about 14%, preferably from about 0.5% to about 10%, and more preferably from about 1% to about 8%, by weight of the shampoo composition.

According to the present invention, suitable fatty amphiphiles, or suitable mixtures of two or more fatty amphiphiles, have a melting point of at least about 27° C. The melting point, as used herein, may be measured by a standard melting point method as described in U.S. Pharmacopeia, USP-NF General Chapter <741> "Melting range or temperature". The melting point of a mixture of two or more materials is determined by mixing the two or more materials at a temperature above the respective melt points and then allowing the mixture to cool. If the resulting composite is a homogeneous solid below about 27° C., then the mixture has a suitable melting point for use in the present invention. A mixture of two or more fatty amphiphiles, wherein the mixture comprises at least one fatty amphiphile having an individual melting point of less than about 27° C., still is suitable for use in the present invention provided that the composite melting point of the mixture is at least about 27° C.

Suitable fatty amphiphiles of the present invention include fatty alcohols, alkoxylated fatty alcohols, fatty phenols, alkoxylated fatty phenols, fatty amides, alkyoxylated fatty amides, fatty amines, fatty alkylamidoalkylamines, fatty alkyoxyalted amines, fatty carbamates, fatty amine oxides, fatty acids, alkoxylated fatty acids, fatty diesters, fatty sorbitan esters, fatty sugar esters, methyl glucoside esters, fatty glycol esters, mono, di & tri glycerides, polyglycerine fatty esters, alkyl glyceryl ethers, propylene glycol fatty acid esters, cholesterol, ceramides, fatty silicone waxes, fatty glucose amides, and phospholipids and mixtures thereof.

In the present invention, the shampoo composition may comprise fatty alcohol gel networks. These gel networks are formed by combining fatty alcohols and surfactants in the ratio of from about 1:1 to about 40:1, from about 2:1 to about 20:1, and/or from about 3:1 to about 10:1. The formation of a gel network involves heating a dispersion of the fatty alcohol in water with the surfactant to a temperature above the melting point of the fatty alcohol. During the mixing process, the fatty alcohol melts, allowing the surfactant to partition into the fatty alcohol droplets. The surfactant brings water along with it into the fatty alcohol. This changes the isotropic fatty alcohol drops into liquid crystalline phase drops. When the mixture is cooled below the chain melt temperature, the liquid crystal phase is converted into a solid crystalline gel network. The gel network contributes a stabilizing benefit to cosmetic creams and hair conditioners. In addition, they deliver conditioned feel benefits for hair conditioners.

The fatty alcohol can be included in the fatty alcohol gel network at a level by weight of from about 0.05 wt % to about 14 wt %. For example, the fatty alcohol may be present in an amount ranging from about 1 wt % to about 10 wt %, and/or from about 6 wt % to about 8 wt %.

The fatty alcohols useful herein include those having from about 10 to about 40 carbon atoms, from about 12 to about 22 carbon atoms, from about 16 to about 22 carbon atoms, and/or about 16 to about 18 carbon atoms. These fatty alcohols can be straight or branched chain alcohols and can be saturated or unsaturated. Non-limiting examples of fatty alcohols include cetyl alcohol, stearyl alcohol, behenyl alcohol, and mixtures thereof. Mixtures of cetyl and stearyl alcohol in a ratio of from about 20:80 to about 80:20 are suitable.

Gel network preparation: A vessel is charged with water and the water is heated to about 74° C. Cetyl alcohol, stearyl alcohol, and SLES surfactant are added to the heated water. After incorporation, the resulting mixture is passed through a heat exchanger where the mixture is cooled to about 35° C. Upon cooling, the fatty alcohols and surfactant crystallized to form a crystalline gel network. Table 1 provides the components and their respective amounts for an example gel network composition.

TABLE 1

| Gel network components | |
|---|---|
| Ingredient | Wt. % |
| Water | 78.27% |
| Cetyl Alcohol | 4.18% |
| Stearyl Alcohol | 7.52% |

TABLE 1-continued

| Gel network components | |
|---|---|
| Ingredient | Wt. % |
| Sodium laureth-3 sulfate (28% Active) | 10.00% |
| 5-Chloro-2-methyl-4-isothiazolin-3-one, Kathon CG | 0.03% |

2. Emusifiers

A variety of anionic and nonionic emulsifiers can be used in the personal care composition of the present invention. The anionic and nonionic emulsifiers can be either monomeric or polymeric in nature. Monomeric examples include, by way of illustrating and not limitation, alkyl ethoxylates, alkyl sulfates, soaps, and fatty esters and their derivatives. Polymeric examples include, by way of illustrating and not limitation, polyacrylates, polyethylene glycols, and block copolymers and their derivatives. Naturally occurring emulsifiers such as lanolins, lecithin and lignin and their derivatives are also non-limiting examples of useful emulsifiers.

3. Chelating Agents

The personal care composition can also comprise a chelant. Suitable chelants include those listed in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996) both incorporated herein by reference. When related to chelants, the term "salts and derivatives thereof" means the salts and derivatives comprising the same functional structure (e.g., same chemical backbone) as the chelant they are referring to and that have similar or better chelating properties. This term include alkali metal, alkaline earth, ammonium, substituted ammonium (i.e. monoethanolammonium, diethanolammonium, triethanolammonium) salts, esters of chelants having an acidic moiety and mixtures thereof, in particular all sodium, potassium or ammonium salts. The term "derivatives" also includes "chelating surfactant" compounds, such as those exemplified in U.S. Pat. No. 5,284,972, and large molecules comprising one or more chelating groups having the same functional structure as the parent chelants, such as polymeric EDDS (ethylenediaminedisuccinic acid) disclosed in U.S. Pat. No. 5,747,440.

Chelating agents can be incorporated in the compositions herein in amounts ranging from 0.001% to 10.0% by weight of the total composition, preferably 0.01% to 2.0%.

Nonlimiting chelating agent classes include carboxylic acids, aminocarboxylic acids, including aminocids, phosphoric acids, phosphonic acids, polyphosponic acids, polyethyleneimines, polyfunctionally-substituted aromatic, their derivatives and salts.

Nonlimiting chelating agents include the following materials and their salts. Ethylenediaminetetraacetic acid (EDTA), ethylenediaminetriacetic acid, ethylenediamine-N, N'-disuccinic acid (EDDS), ethylenediamine-N,N'-diglutaric acid (EDDG), salicylic acid, aspartic acid, glutamic acid, glycine, malonic acid, histidine, diethylenetriaminepentaacetate (DTPA), N-hydroxyethylethylenediaminetriacetate, nitrilotriacetate, ethylenediaminetetrapropionate, triethylenetetraaminehexaacetate, ethanoldiglycine, propylenediaminetetracetic acid (PDTA), methylglycinediacetic acid (MODA), diethylenetriaminepentaacetic acid, methylglycinediacetic acid (MGDA), N-acyl-N,N',N'-ethylenediaminetriacetic acid, nitrilotriacetic acid, ethylenediaminediglutaric acid (EDGA), 2-hydroxypropylenediamine disuccinic acid (HPDS), glycinamide-N,N'-disuccinic acid (GADS), 2-hydroxypropylenediamine-N—N'-disuccinic acid (HPDDS), N-2-hydroxyethyl-N,N-diacetic acid, glyceryliminodiacetic acid, iminodiacetic acid-N-2-hydroxypropyl sulfonic acid, aspartic acid N-carboxymethyl-N-2-hydroxypropyl-3-sulfonic acid, alanine-N,N'-diacetic acid, aspartic acid-N,N'-diacetic acid, aspartic acid N-monoacetic acid, iminodisuccinic acid, di amine-N,N'-dipoly acid, mono amide-N,N'-dipolyacid, diaminoalkyldi(sulfosuccinic acids) (DDS), ethylenediamine-N—N'-bis (ortho-hydroxyphenyl acetic acid)), N,N'-bis(2-hydroxybenzyl)ethylenediamine-N,N'-diacetic acid, ethylenediaminetetraproprionate, triethylenetetraaminehexacetate, diethylenetriaminepentaacetate, dipicolinic acid, ethylenedicysteic acid (EDC), ethylenediamine-N,N'-bis(2-hydroxyphenylacetic acid) (EDDHA), glutamic acid diacetic acid (GLDA), hexadentateaminocarboxylate (HBED), polyethyleneimine, 1-hydroxydiphosphonate, aminotri(methylenephosphonic acid) (ATMP), nitrilotrimethylenephosphonate (NTP), ethylenediaminetetramethylenephosphonate, diethylenetriaminepentamethylenephosphonate (DTPMP), ethane-1-hydroxydiphosphonate (HEDP), 2-phosphonobutane-1,2,4-tricarboxylic acid, polyphosphoric acid, sodium tripolyphosphate, tetrasodium diphosphate, hexametaphosphoric acid, sodium metaphosphate, phosphonic acid and derivatives, Aminoalkylen-poly (alkylenphosphonic acid), aminotri(1-ethylphosphonic acid), ethylenediaminetetra(1-ethylphosphonic acid), aminotri(1-propylphosphonic acid), aminotri(isopropylphosphonic acid), ethylenediaminetetra(methylenephosphonic acid) (EDTMP), 1,2-dihydroxy-3,5-disulfobenzene.

Aqueous Carrier

The personal care compositions can be in the form of pourable liquids (under ambient conditions). Such compositions will therefore typically comprise a carrier, which is present at a level of from about 40% to about 85%, alternatively from about 45% to about 80%, alternatively from about 50% to about 75% by weight of the personal care composition. The carrier may comprise water, or a miscible mixture of water and organic solvent, and in one aspect may comprise water with minimal or no significant concentrations of organic solvent, except as otherwise incidentally incorporated into the composition as minor ingredients of other essential or optional components.

The carrier useful in the personal care compositions of the present invention may include water and water solutions of lower alkyl alcohols and polyhydric alcohols. The lower alkyl alcohols useful herein are monohydric alcohols having 1 to 6 carbons, in one aspect, ethanol and isopropanol. Exemplary polyhydric alcohols useful herein include propylene glycol, hexylene glycol, glycerin, and propane diol.

G. Foam Dispenser

The personal care composition described herein may be provided in a foam dispenser. The foam dispenser may be an aerosol foam dispenser. The aerosol foam dispenser may comprise a reservoir for holding the personal care treatment composition. The reservoir may be made out of any suitable material selected from the group consisting of plastic, metal, alloy, laminate, and combinations thereof. The reservoir may be for one-time use. The reservoir may be removable from the aerosol foam dispenser. Alternatively, the reservoir may be integrated with the aerosol foam dispenser. And there may be two or more reservoirs.

The foam dispenser may also be a mechanical foam dispenser. The mechanical foam dispenser described may be selected from the group consisting of squeeze foam dispensers, pump foam dispensers, other mechanical foam dispensers, and combinations thereof. The mechanical foam dispenser may be a squeeze foam dispenser. Non-limiting examples of suitable pump dispensers include those described in WO 2004/078903, WO 2004/078901, and WO 2005/078063 and may be supplied by Albea (60 Electric Ave., Thomaston, CT 06787 USA) or Rieke Packaging Systems (500 West Seventh St., Auburn, Indiana 46706).

The mechanical foam dispenser may comprise a reservoir for holding the personal care treatment composition. The reservoir may be made out of any suitable material selected from the group consisting of plastic, metal, alloy, laminate, and combinations thereof. The reservoir may be a refillable reservoir such as a pour-in or screw-on reservoir, or the reservoir may be for one-time use. The reservoir may also be removable from the mechanical foam dispenser. Alternatively, the reservoir may be integrated with the mechanical foam dispenser. And there may be two or more reservoirs.

The reservoir may be comprised of a material selected from the group consisting of rigid materials, flexible materials, and combinations thereof. The reservoir may be comprised of a rigid material if it does not collapse under external atmospheric pressure when it is subject to an interior partial vacuum.

H. Product Form

The personal care compositions of the present invention may be presented in typical personal care formulations. They may be in the form of solutions, dispersion, emulsions, powders, talcs, encapsulated, spheres, spongers, solid dosage forms, foams, and other delivery mechanisms. The compositions of the present invention may be hair tonics, leave-on hair products such as treatment, and styling products, rinse-off hair products such as shampoos and personal cleansing products, and treatment products; and any other form that may be applied to hair.

I. Applicator

In the present invention, the personal care composition may be dispensed from an applicator for dispensing directly to the scalp area. Dispensing directly onto the scalp via a targeted delivery applicator enables deposition of the non-diluted cleaning agents directly where the cleaning needs are highest. This also minimizes the risk of eye contact with the cleansing solution.

The applicator is attached or can be attached to a bottle containing the cleansing personal care composition. The applicator can consist of a base that holds or extends to a single or plurality of tines. The tines have openings that may be at the tip, the base or at any point between the tip and the base. These openings allow for the product to be distributed from the bottle directly onto the hair and/or scalp.

Alternatively, the applicator can also consist of brush-like bristles attached or extending from a base. In this case product would dispense from the base and the bristles would allow for product distribution via the combing or brushing motion.

Applicator and tine design and materials can also be optimized to enable scalp massage. In this case it would be beneficial for the tine or bristle geometry at the tips to be more rounded similar to the roller ball applicator used for eye creams. It may also be beneficial for materials to be smoother and softer; for example metal or metal-like finishes, "rubbery materials".

J. Methods

Viscosity Measurement

Shampoo viscosities can be measured on a 2.5 mL sample using a cone and plate Brookfield RS rheometer with cone C75-1 at constant shear rate of 2 $s^{-1}$, at 27° C. at 3 mins. The personal care composition of the present invention may have a viscosity of >about 5000 cps (centipoise); the personal care composition may have a viscosity of from about 5000 to about 20000 cps; the personal care composition may have a viscosity of from about 6000 to about 15000 cps; the personal care composition may have a viscosity of from about 7000 to about 10000 cps.

TEST METHODS

In Vivo Scalp Depo

The on-scalp deposition of the anti-dandruff active is measured by having the hair of individuals washed with a composition comprising an anti-dandruff active, for example a composition pursuant to the present invention. A trained cosmetician will dose the liquid shampoo control at 5 g on ½ of the panelist scalp and wash according to conventional washing protocol. Then 5 g of test shampoo is dosed to the other half of the panelist head and washed according to a conventional washing protocol. The hair is then parted on an area of the scalp to allow an open-ended glass cylinder to be held on the surface while an aliquot of an extraction solution is added and agitated prior to recovery and analytical determination of anti-dandruff active content by conventional methodology, such as HPLC.

Measurement of Active Deposition

The concentration of the agent in the ethanol extraction solvent is measured by HPLC. Quantitation is made by reference to a standard curve. The concentration detected by HPLC is converted into an amount collected in grams by using the concentration multiplied by volume.

The deposition efficiency can be calculated using the following equation. The area of the scalp extracted in each case is held constant:

$$\text{Deposition efficiency} = \frac{\text{mass agent deposited by example formula}}{\text{mass agent deposited by control formula}}$$

Sample calculation for deposition efficiency, where:
Mass of ZPT deposited by example formula=1.0 ug
Mass of ZPT deposited by control formula=0.5 ug Deposition efficiency=1.0/0.5

Deposition efficiency=2×

In Vivo Fungal Efficacy Testing

Subjects from all test groups will have Baseline scalp swabs for measurement of scalp *Malassezia*. Subjects will take home a test product(s) and will be instructed on use test products throughout the week. The test concludes at week 2 with panelists scalps being swabbed and samples collected. *Malassezia* is quantified from scalp surface swabs via qPCR. The change in *Malassezia* amount across time will be reported as fungal reduction overtime.

Preparation of the Deposition Control

Deposition control compositions are prepared by creating a formulation with zinc pyrithione and zinc carbonate in sulfated surfactants. The formulation is adjusted to about pH 7. For example, the formulation shown as Example J is the deposition control and fungal efficacy testing composition for the test compositions A through I.

Non-Limiting Examples

The shampoo compositions illustrated in the following examples are prepared by conventional formulation and mixing methods. All exemplified amounts are listed active wt. percent and exclude minor materials such as diluents, preservatives, color solutions, imagery ingredients, botanicals, and so forth, unless otherwise specified.

Preparation of the Example Shampoos Compositions

The example cleaning compositions are prepared by combining the surfactant(s), polymers, the antidandruff active, preservatives, and the remainder of the water with ample agitation to ensure a homogenous mixture. The mixture can be heated to 65-75° C. to speed the solubilization of the surfactants, then cooled. Product pH is then adjusted as necessary to create thickening and resulting of approximately a pH of 5-7.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

| Example compositions | A | B | C | D | E |
|---|---|---|---|---|---|
| Sodium Laureth Sulfate (SLE1S) (1) | | | | | |
| Sodium Lauryl Sulfate (2) | | | | | |
| Sodium Cocoyl isethionate (3) | 6 | 6 | 6 | 6 | 6 |
| Sodium Lauroyl methyl isethionate (4) | | | | | |
| Sodium Lauroyl Sarcosinate (5) | 4 | 4 | 4 | 4 | 4 |
| Lauramidopropyl Betaine (6) | 9.75 | 9.75 | 9.75 | 9.75 | 9.75 |
| Cocamidopropyl Betaine (7) | | | | | |
| Cocamide MEA (8) | | | | | |
| Acrylate copolymer (9) | 0.7 | 0.7 | 0.7 | 0.7 | 0.7 |
| Glycol Distearate (10) | | | | | |
| Zinc Pyrithione (11) | 2 | 1 | 2 | 1 | 2 |
| Zinc Carbonate (12) | | | | | |

-continued

| | | | | | |
|---|---|---|---|---|---|
| Polyquaternium-10~1.8 Mil MW, 0.7 CD (13) | 0.6 | 0.6 | 0.6 | 0.6 | 0.25 |
| Guar Hyrdroxypropyltrimonium Chloride (LMW) ~500K MW, 0.7 CD (14) | | | | | |
| Guar Hyrdroxypropyltrimonium Chloride BF17 (HMW)~800K MW, 1.5 CD (15) | | | | | |
| Polyquaternium-76 (16) | | | | | |
| Perfume (17) | 1 | 1 | 1 | 1 | 1 |
| Dimethicone DC 1872 (18) | 0.5 | 0.5 | 0.5 | 0.5 | 0 |
| Dimethicone DC330M (19) | | | | | |
| citric acid (20) | QS to pH 5 | QS to pH 5 | QS to pH 5.8 | QS to pH 5.8 | QS to pH 5 |
| Hydrochloric acid (21) | | | | | |
| Methylchloroisothiazolinone/Methylisothiazolinone (Kathon) (22) | | | | | |
| Sodium Salicylate (23) | 0.15 | 0.15 | 0.15 | 0.15 | 0.15 |
| Sodium Chloride (24) | | | | | |
| Sodium Benzoate (25) | 0.25 | 0.25 | 0.25 | 0.25 | 0.25 |
| Water and Minors (QS to 100%) (26) | QS | QS | QS | QS | QS |
| Deposition efficiency | 6X | 3X | 8X | 4X | 3X |
| Actual fungal Efficacy vs. potentiated ZPT control (95% conf interval) *significantly up +, parity = | + | = | | | + |
| ZPT Deposition ≥ 3X vs. Potentiated Control may result in parity to increased fungal efficacy *significantly up ++, parity =, − Significantly down | ++ | = | =/+ | =/+ | ++ |

| Example compositions | F | G | H | I | J |
|---|---|---|---|---|---|
| Sodium Laureth Sulfate (SLE1S) (1) | | | | | 10.5 |
| Sodium Lauryl Sulfate (2) | | | | | 1.5 |
| Sodium Cocoyl isethionate (3) | 6 | 6 | 6 | 6 | |
| Sodium Lauroyl methyl isethionate (4) | | | | | |
| Sodium Lauroyl Sarcosinate (5) | 4 | 4 | | 4 | |
| Lauramidopropyl Betaine (6) | 9.75 | 9.75 | 9.75 | 9.75 | |
| Cocamidopropyl Betaine (7) | | | | | 1 |
| Cocamide MEA (8) | | | | | 1 |
| Acrylate copolymer (9) | 0.7 | 0.7 | 0.7 | 0.7 | |
| Glycol Distearate (10) | | | | | 1.5 |
| Zinc Pyrithione (11) | 1 | 1 | 1 | 1 | 1 |
| Zinc Carbonate (12) | | | | | 1.61 |
| Polyquaternium-10~1.8 Mil MW, 0.7 CD (13) | 0 | | 0.6 | | |
| Guar Hyrdroxypropyltrimonium Chloride (LMW) ~500K MW, 0.7 CD (14) | | 0.6 | | | 0.3 |
| Guar Hyrdroxypropyltrimonium Chloride BF17 (HMW)~800K MW, 1.5 CD (15) | | | | 0.6 | |
| Polyquaternium-76 (16) | | | | | 0.01 |
| Perfume (17) | 1 | 1 | 1 | 1 | 0.85 |
| Dimethicone DC 1872 (18) | 0.5 | 0.5 | 0 | 0.5 | |
| Dimethicone DC330M (19) | | | | | 0.8 |
| citric acid (20) | QS to pH 5.2 | QS to pH 5.5 | QS to pH 5.0 | QS to pH 5.5 | |
| Hydrochloric acid (21) | | | | | QS to pH 7 |
| Methylchloroisothiazolinone/Methylisothiazolinone (22) | | | | | 0.033 |
| Sodium Salicylate (23) | 0.15 | 0.15 | 0.15 | 0.15 | |
| Sodium Chloride (24) | | | | | 1 |
| Sodium Benzoate (25) | 0.25 | 0.25 | 0.25 | 0.25 | 0.15 |
| Water and Minors (QS to 100%) (26) | QS | QS | QS | QS | QS |

-continued

| | | | | | |
|---|---|---|---|---|---|
| Deposition efficiency | 0.3X | 0.6X | 3X | 7X | 0.9 |
| Actual fungal Efficacy vs. potentiated ZPT control (95% conf interval) *significantly up +, parity = | | | | | Control |
| ZPT Deposition ≥ 3X vs. Potentiated Control may result in parity to increased fungal efficacy *significantly up ++, parity =, − Significantly down | − | − | =/+ | =/+ | |

Key
1. Sodium Laureth Sulfate from P&G Chemicals
2. Sodium Lauryl Sulfate from Stepan Company
3. Sodium Cocoyl isethionate from Innospec
4. Sodium Lauroyl methyl isethionate from Innospec
5. Sodium Lauroyl Sarcosinate from Croda
6. Lauramidopropyl Betaine less than 1% NaCl from Solvay
7. Cocamidopropyl Betaine less than 1% NaCl from Evonik
8. Cocamide MEA from Stepan
9. Acrylate copolymer from BASF
10. Glycol Distearate from Golschmidt Chemical Company
11. Zinc Pyrithione from Lonza
12. Zinc Carbonate from Bruggeman Group
13. Polyquatemium-10~1.8 Mil MW, 0.7 CD from Dow
14. Guar Hyrdroxypropyltrimonium Chloride (LMW)~500K MW, 0.7 CD from Ashland
15. Guar Hyrdroxypropyltrimonium Chloride BF17 (HMW)~800K MW, 1.5 CD from Ashland
16. Polyquatemium-76 from Solvay
17. Perfume from Givuadan
18. Dimethicone DC 1872 from Dow
19. Dimethicone DC330M from Dow
20. Citric acid from Acher Daniels Midland
21. Hydrochloric acid from Mallinckrodt Baker Inc.
22. Methylchloroisothiazolinone/Methylisothiazolinone (Kathon) from Rohm and Haas
23. Sodium Salicylate from Novacyl
24. Sodium Chloride from Morton
25. Sodium Benzoate from Kalama Chemical
26. Water and Minors (QS to 100%) from Misty Mountain Spring water

OTHER EXAMPLES

| Example compositions | K | L | M | N | O |
|---|---|---|---|---|---|
| Sodium Laureth Sulfate (SLE1S) (1) | | | | | |
| Sodium Lauryl Sulfate (2) | | | | | |
| Sodium Cocoyl isethionate (3) | | | | 6 | 6 |
| Sodium Lauroyl methyl isethionate (4) | 6 | 6 | 6 | | |
| Sodium Lauroyl Sarcosinate (5) | 4 | | | 4 | 4 |
| Lauramidopropyl Betaine (6) | 9.75 | 10.75 | 9.75 | | |
| Cocamidopropyl Betaine (7) | | | | 9.75 | 9.75 |
| Cocamide MEA (8) | | | | | |
| Acrylate copolymer (9) | 0.7 | 0.7 | 0.7 | 0.7 | 0.7 |
| Trihydroxystearin (10) | | | | | |
| Glycol Distearate (11) | | | | | |
| Zinc Pyrithione (12) | 2 | 2 | 1 | 2 | 1 |
| Sulfur (13) | | | | | |
| Zinc Carbonate (14) | | | | | |
| Polyquaternium-10 (15) | 0.6 | 0.6 | 0.6 | 0.6 | 0.25 |
| Guar Hyrdroxypropyltrimonium Chloride (LMW) (16) | | | | | |
| Guar Hyrdroxypropyltrimonium Chloride BF17 (HMW) (17) | | | | | |
| Polyquaternium-76 (18) | | | | | |
| Perfume (19) | 1 | 1 | 1 | 1 | 1 |
| Dimethicone DC 1872 (20) | 0.5 | 0.5 | 0.5 | 0.5 | 0.5 |
| Dimethicone DC330M (21) | | | | | |
| citric acid (22) | QS to pH 5 | QS to pH 5 | QS to pH 5.8 | QS to pH 5.8 | QS to pH 5.8 |
| Hydrochloric acid (23) | | | | | |
| Methylchloroisothiazolinone/Methylisothiazolinone (24) | | | | | |
| Sodium Salicylate (25) | 0.15 | 0.15 | 0.15 | 0.15 | 0.15 |
| Sodium Chloride (26) | | | | | |
| Sodium Benzoate (27) | 0.25 | 0.25 | 0.25 | 0.25 | 0.25 |
| Water and Minors (QS to 100%) (28) | QS | QS | QS | QS | QS |

-continued

| Example compositions | P | Q | R | S | T |
|---|---|---|---|---|---|
| Sodium Laureth Sulfate (SLE1S) (1) | | | | | |
| Sodium Lauryl Sulfate (2) | | | | | |
| Sodium Cocoyl isethionate (3) | 6 | 6 | 6 | 6 | |
| Sodium Lauroyl methyl isethionate (4) | 6 | | | | |
| Sodium Lauroyl Sarcosinate (5) | | 4 | 4 | 4 | |
| Lauramidopropyl Betaine (6) | | | | | |
| Cocamidopropyl Betaine (7) | 9.75 | 9.75 | 9.75 | 9.75 | 9.75 |
| Cocamide MEA (8) | | | | | |
| Acrylate copolymer (9) | 0.7 | 0.7 | 0.7 | 0.1 | 0.7 |
| Trihydroxystearin (10) | | | | | |
| Glycol Distearate (11) | | | | | |
| Zinc Pyrithione (12) | 1 | 1 | 1 | 1 | 1 |
| Sulfur (13) | | | | | |
| Zinc Carbonate (14) | | | | | |
| Polyquaternium-10 (15) | 0.6 | | | | |
| Guar Hyrdroxypropyltrimonium Chloride (LMW) (16) | | 1.2 | | 1.2 | |
| Guar Hyrdroxypropyltrimonium Chloride BF17 (HMW) (17) | | | 0.6 | | 0.6 |
| Polyquaternium-76 (18) | | | | | |
| Perfume (19) | 1 | 1 | 1 | 1 | 1 |
| Dimethicone DC 1872 (20) | 0.5 | 0 | 0 | 0.5 | 0 |
| Dimethicone DC330M (21) | | | | | |
| citric acid (22) | QS to pH 5.8 | QS to pH 5.8 | QS to pH 5.8 | to pH 5.8 | to pH 5.8 |
| Hydrochloric acid (23) | | | | | |
| Methylchloroisothiazolinone/Methylisothiazolinone (24) | | | | | |
| Sodium Salicylate (25) | 0.15 | 0.15 | 0.15 | 0.15 | 0.15 |
| Sodium Chloride (26) | | | | | |
| Sodium Benzoate (27) | 0.25 | 0.25 | 0.25 | 0.25 | 0.25 |
| Water and Minors (QS to 100%) (28) | QS | QS | QS | QS | QS |

| Example compositions | U | V | W | X | Y | Z | A1 |
|---|---|---|---|---|---|---|---|
| Sodium Laureth Sulfate (SLE1S) (1) | | | | | | | |
| Sodium Lauryl Sulfate (2) | | | | | | | |
| Sodium Cocoyl isethionate (3) | 6 | 6 | | | | | 6 |
| Sodium Lauroyl methyl isethionate (4) | | | 6 | 6 | 6 | 6 | |
| Sodium Lauroyl Sarcosinate (5) | 4 | 4 | 4 | 4 | 4 | 4 | 4 |
| Lauramidopropyl Betaine (6) | 9.75 | 9.75 | 9.75 | 9.75 | 9.75 | 9.75 | 9.75 |
| Cocamidopropyl Betaine (7) | | | | | | | |
| Cocamide MEA (8) | | | | | | | |
| Acrylate copolymer (9) | 0.1 | 0.1 | 0.1 | 0.1 | 0.1 | 0.1 | 1.2 |
| Trihydroxystearin (10) | | | | | 0.1 | 0.2 | |
| Glycol Distearate (11) | | | 1.5 | 1.5 | | | |
| Zinc Pyrithione (12) | 1 | 1 | 2 | 1 | 2 | 1 | |
| Sulfur (13) | | | | | | | 5 |
| Zinc Carbonate (14) | | | 1.61 | 1.61 | 1.61 | 1.61 | |
| Polyquaternium-10 (15) | | | 0.6 | 0.6 | 0.6 | 0.6 | 0.6 |
| Guar Hyrdroxypropyltrimonium Chloride (LMW) (16) | 1.2 | | | | | | |
| Guar Hyrdroxypropyltrimonium Chloride BF17 (HMW) (17) | | 0.6 | | | | | |
| Polyquaternium-76 (18) | | | | | | | |
| Perfume (19) | 1 | 1 | 1 | 1 | 1 | 1 | 1 |
| Dimethicone DC 1872 (20) | 0.5 | 0.5 | | 1 | | 1 | 1 |
| Dimethicone DC330M (21) | | | 1 | 1 | | | |
| citric acid (22) | to pH 5.8 | to pH 5.8 | | | | | |
| Hydrochloric acid (23) | | | QS to pH 7 | QS to pH 7 | QS to pH 7 | QS to pH 7 | QS to pH 7 |
| Methylchloroisothiazolinone/Methylisothiazolinone (24) | | | | | | | |
| Sodium Salicylate (25) | 0.15 | 0.15 | 0.15 | 0.15 | 0.15 | 0.15 | 0.15 |
| Sodium Chloride (26) | | | | | | | |
| Sodium Benzoate (27) | 0.25 | 0.25 | 0.25 | 0.25 | 0.25 | 0.25 | 0.25 |
| Water and Minors (QS to 100%) (28) | QS | QS | QS | QS | QS | QS | QS |

| Example composition | B1 Comparable | C1 Comparable |
|---|---|---|
| Zinc Pyrithione (11) | 2 | 1 |
| Deposition efficiency | 0.6X | 0.3X |
| Actual fungal Efficacy vs. potentiated ZPT control (95% conf interval) *significantly up +, parity = ZPT Deposition ≥ 3X vs. Potentiated Control may result in parity to increased fungal efficacy *significantly up ++, parity =, – Significantly down | – | – |

Key
1. Sodium Laureth Sulfate from P&G Chemicals
2. Sodium Lauryl Sulfate from Stepan Company
3. Sodium Cocoyl isethionate from Innospec
4. Sodium Lauroyl methyl isethionate from Innospec
5. Sodium Lauroyl Sarcosinate from Croda
6. Lauramidopropyl Betaine less than 1% NaCl from Solvay
7. Cocamidopropyl Betaine less than 1% NaCl from Evonik
8. Cocamide MEA from Stepan
9. Acrylate copolymer from BASF
10. Trihydroxystearin from Elementis
11. Glycol Distearate from Goldschmidt Chemical Company
12. Zinc Pyrithione from Lonza
13. Sulfur from Solvay
14. Zinc Carbonate from Bruggeman Group
15. Polyquaternium-10 from Dow
16. Guar Hyrdroxypropyltrimonium Chloride (LMW)~500 k MW, 0.7 CD from Ashland
17. Guar Hyrdroxypropyltrimonium Chloride BF17 (HMW)~800 k MW, 1.5 CD from Ashland
18. Polyquaternium-76 from Solvay
19. Perfume from Givuadan
20 Dimethicone DC 1872 from Dow
21. Dimethicone DC330M from Dow
22. Citric acid from Acher Daniels Midland
23. Hydrochloric acid from Mallinckrodt Baker Inc.
24. Methylchloroisothiazolinone/Methylisothiazolinone (Kathon) from Rohm and Haas
25. Sodium Salicylate from Novacyl
26. Sodium Chloride from Morton
27. Sodium Benzoate from Kalama Chemical
28. Water and Minors (QS to 100%) from Misty Mountain Spring water Results/Discussion It has been identified that formula A and B at 2% ZPT and 1% ZPT respectively at a pH of 5.0 resulted in 6× and 3× deposition vs. potentiated control formula J. The resulting efficacy for formula A is significantly up vs. the potentiated control formula J. This identified that formula A at the higher concentration of 2% ZPT and resulting 6× depo translated to significantly increased fungal reduction from consumer scalp swab results. Formula B at 3× deposition efficiency only resulted in parity to the potentiated control formula J. This indicates that 3× of non-potentiated deposited ZPT is required to reach that of potentiated ZPT formula control J.

Formula C and D are comparable to A and B from a ZPT concentration but differ from resulting final pH. Formula A and B are pH of 5 and formula C and D are pH of 5.8. The resulting change in pH resulted in a significant increase in deposition to 6× for Formula A at pH 5 and 8× for Formula C at pH 5.8. The same increasing trend in deposition existed for the 1% ZPT formulas B and D which shows 3× depo at pH 5 for formula B and 4× depo at pH 5.8 for formula D. This result in increased deposition via increased pH is surprising because it is expected that lower pH, more protonation, which increases thickening and adhesive nature of the anionic polymer is hypothesized to help deposit negatively charged ZPT more effectively.

Formula E which contains less cationic polymer polyquaternium-10 at 0.25% shows less deposition at 3× vs. formula A at 0.6%. It is observed though, that the resulting fungal efficacy for formula E resulted in significantly up, similar to formula A result, vs. the potentiated control. Overall formula E is similar in fungal efficacy of formula A. This is also surprising as it is expected that deposition level would correlate with fungal efficacy, but this does not seem to be the case. This result indicates that the resulting phase that may be generated via the lower cationic polymer level in formula E could provide more bioavailable ZPT than formula A.

Formula F, containing no cationic polymer and low anionic polymer at 0.7% shows significantly decreased deposition of 0.3×. This result is similar to a commercial sulfate free market formula B1 at 0.6× which indicate on back ingredient label list that no cationic polymer is present and similar to a commercial sulfate free market formula C1 which contains a synthetic polymer polyquaternium-39. This highlights that a cationic polymer and anionic polymer are necessary in the ZPT non-potentiated formulation to deposit significant levels of ZPT which would lead to fungal efficacy similar to potentiated ZPT formulations. It also indicates that cationic polymers such as Polyquaternium-10 or Guar hydroxypropyltrimonium chloride which are very hydrophilic are better cationic polymer options vs. synthetic more hydrophobic polymers such as polyquaternium-39.

Formula G results in 0.6× deposition when low molecular weight ~500K MW and 0.7 meq/g charge density cationic polymer Guar is present at 0.6%. This formulation G would be expected to be less efficacious vs. potentiated control due to the low amount of deposition observed. Although, it may be hypothesized that increasing the concentration to ~1.2% of this ~500 k MW cationic polymer will increase the ZPT deposition to at least a 3× depo efficiency. This is consistent with previous observations, formula A and D comparison, that increasing the concentration of cationic polymer will increase the scalp deposition of active. Formula H results in 3× deposition when higher molecular weight ~1.8 Mil MW and 0.7 meq/g charge density cationic polymer cellulose is present at 0.6%. Formula I result in 7× deposition when high molecular weight ~800K MW and 1.5 meq/g charge density. These results indicate that hydrophilic high molecular weight cationic polymers and mid to high charge density (0.7-1.5 meq/g) are important for the increased deposition of ZPT to scalp and hair. The results also reinforce that increasing concentration of the cationic polymer will also increase deposition of ZPT to scalp and hair.

In the present invention, in the personal care composition there may be a greater to or equal to 3× deposition efficiency when compared to a potentiated control.

In the present invention, in the personal care composition there may be wherein 1% of a scalp active results in an equal or greater deposition efficiency when compared to a 2% scalp active.

Consumer Test Method 1. Example D. Vs. Comparable C1 Sulfate Free Comparison Sequential Monadic Test, 2 legs used 2 weeks each. Questionnaire after each leg plus preference at the end.

Recruited consumers who consider themselves to suffer from light, moderate, or severe dandruff. The consumers also must be sulfate free users. The test is not branded. A 50/50 male and female group of approximately 200 panelists are recruited. The shampoo tested includes example D and comparable C1. The data is analyzed at 90% and 80% confidence.

| Example composition | B1 Comparable | C1 Comparable | Example D |
|---|---|---|---|
| Zinc Pyrithione (11) | 2 | 1 | 1 |
| Deposition efficiency | 0.6X | 0.3X | 4X |
| Actual fungal Efficacy vs. t (95% conf interval) *significantly up +, parity = | | | |
| ZPT Deposition ≥ 3X vs. Potentiated Control may result in parity to increased fungal efficacy *significantly up ++, parity =, – Significantly down | – | – | =/+ |

| Consumer test 1. results | B1 Comparable | C1 Comparable | Example D |
|---|---|---|---|
| Overall rating of sulfate free shampoo Antidandruff shampoo (90% Conf) | NA | | |
| Overall cleaning (90% Conf) | NA | | |
| Leaving scalp feeling clean (90% Conf) | NA | | |
| Overall health of my scalp (90% Conf) | NA | | |
| Reducing scalp itch (90% Conf) | NA | | |
| Providing soothing feeling to the scalp (90% Conf) | NA | | |
| Providing you with effective scalp care (ie Dandruff, Dryness, Itch, oiliness) (80% Conf) | NA | | |

Example D sulfate free antidandruff shampoo compared to C1 comparative sulfate free antidandruff shampoo containing the same level of AD active at 1% shows significant consumer responses to questions regarding overall preference, cleaning, scalp health, itch, smoothing, and effective scalp care. These are all indications that the increase deposition of Antidandruff active in example D is delivering noticeable consumer scalp benefits vs a comparable marketed sulfate free antidandruff shampoo with the same level of AD active.

| Key | Not tested | Sig down vs. example | Sig up vs. comparable | Parity to comparable |
|---|---|---|---|---|
| *Results Difference at 90% or 80% confidence | NA | | | |

*Confidence interval is called out from reported data

Consumer Test Method 2. Example D Sulfate Free Vs. Potentiated Marketed Control Product Comparable D1

Sequential Monadic "paired" Test (complete block design), 2-week usage each, assessment after each product use, and preference subset at the end. A 50/50 male and female group of approximately 100 panelists is recruited. This is in an antidandruff shampoo context only. Consumers are recruited based on being users of antidandruff products within the past 3 months. The data is analyzed at 90% and 80% confidence.

| Example composition | D1 Comparable | Example D |
|---|---|---|
| Zinc Pyrithione (11) | 1 | 1 |
| Zinc Carbonate (14) | 1.6 | |
| Deposition efficiency | 1X | 4X |
| Actual fungal Efficacy vs. potentiated ZPT control (95% conf interval) *significantly up +, parity = | | |
| ZPT Deposition ≥ 3X vs. Potentiated Control may result in parity to increased fungal efficacy *significantly up ++, parity =, – Significantly down | = | =/+ |

| Consumer test 2. results | D1 Comparable | Example D |
|---|---|---|
| Overall rating (90% Conf) | | |
| Overall cleaning (90% Conf) | | |
| Leaving scalp feeling clean (90% Conf) | | |
| Overall health of my scalp (90% Conf) | | |
| Being Gentle on your scalp (90% Conf) | | |
| Providing you with effective scalp care (ie Dandruff, Dryness, Itch, oiliness) (80% Conf) | | |

Example D sulfate free antidandruff shampoo, with 1% ZPT concentration, when compared to a potentiated D1 comparative sulfated antidandruff shampoo, with 1% ZPT concentration, in a consumer evaluation has resulted in parity to significant consumer responses to questions regarding overall rating, cleaning, scalp health, gentle, and effective scalp care. These are all indications that the increase deposition of Antidandruff active in example D is at least comparable to significantly up for consumer scalp benefits vs a potentiated sulfated antidandruff shampoo.

In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minors will vary depending on the physical and chemical characteristics of the particular ingredients selected to make the personal care composition.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular descriptions of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care composition comprising:
   a) from about 15% to about 22% of one or more sulfate free surfactants wherein the one or more sulfate free surfactants is a mixture of sodium cocoyl isethionate, sodium lauroyl methyl isethionate and sodium lauroyl sarcosinate;
   b) from about 0.1% to about 10% of one or more scalp active wherein the scalp active is zinc pyrithione;
   c) from about 0.1% to about 1.2% of a cationic polymers having a molecular weight in the range of from about 50,000 to less than or equal to about 1.8 million and a charge density of about 0.5 to about 1.7 meq/g;
   d) from about 0.1% to about 1.2% of a rheology modifier wherein the rheology modifier is an alkali swellable emulsion polymer and having a pH of about 5 to about 7 and having a viscosity of >about 5000 cps; wherein the personal care composition is free of sulfate surfactant and wherein there is a greater to or equal to 3× deposition efficiency when compared to a potentiated control wherein the potentiated control comprises zinc pyrithione and zinc carbonate in sulfated surfactants at a pH of about 7.

2. The personal care composition according to claim 1 wherein the rheology modifier is present from about 0.4% to about 0.8%.

3. The personal care composition according to claim 1 wherein the rheology modifier is present from about 0.5% to about 0.7%.

4. The personal care composition according to claim 1 wherein the one or more surfactants is from about 16% to about 20%.

5. The personal care composition according to claim 1 wherein the one or more surfactants is from about 17% to about 20%.

6. The personal care composition according to claim 1 wherein the rheology polymer is combined with one or more of the group consisting of polyvinylpyrrolidone, crosslinked polyvinylpyrrolidone and derivatives, polyvinylalcohol and derivatives, polyethyleneimine and derivatives, alginic acid based matertials, polyurethane polymers, associative polymeric thickeners, cellulose and derivatives, a guar and guar derivatives, polyethylene oxide, polypropylene oxide, POE-PPO copolymers, polyalkylene glycols, silicas, water-swellable clays, gums, dibenzylidene sorbitol, karaggenan, pectin, agar, quince seed (*Cydonia oblonga* Mill), starch, starch-derivatives algae extracts, dextran, succinoglucan, and pulleran and mixtures thereof.

7. The personal care composition according to claim 1 wherein the cationic polymer is present from about 0.2% to about 1%.

8. The personal care composition according to claim 1, wherein the cationic polymer is present from about 0.6% to about 0.9%.

9. The personal care composition according to claim 1, wherein the cationic polymer has a molecular weight of from about 100,000 to about 1 million.

10. The personal care composition according to claim 1, wherein the cationic polymer has a molecular weight of from about 500,000 to about 1.2 million.

11. The personal care composition according to claim 1, wherein the cationic polymer has a charge density of from about 0.6 to about 1.2 meq/g.

12. The personal care composition according to claim 1, wherein the cationic polymer has a charge density of from about 0.8 to about 1.0 meq/g.

13. The personal care composition according to claim 1 further comprising from about 0.25% to about 15% of one or more amphoteric, nonionic or zwitterionic co-surfactants.

14. The personal care composition according to claim 1 wherein the scalp active is from about 2% to about 5%.

15. The personal care composition according to claim 1 wherein the scalp active is from about 1% to about 2%.

16. The personal care composition according to claim 1 wherein the pH of the composition is from about 5.5 to about 6.5.

17. The personal care composition according to claim 16 wherein the pH of the composition is from about 5.8 to about 6.

18. The personal care composition according to claim 1 wherein the composition further comprises a gel network.

19. The personal care composition according to claim 1 wherein the composition further comprises a conditioning agent.

20. The personal care composition according to claim 19 wherein the conditioning agent is a silicone.

21. The personal care composition according to claim 1 further comprising one or more scalp health agent.

22. The personal care composition according to claim 21 wherein the scalp health agent is salicylic acid.

23. The personal care composition according to claim 21 wherein the scalp health agent is menthol and/or menthyl lactate.

24. The personal care composition according to claim 1 further comprising from about 0.5% to about 7% of a perfume.

* * * * *